US012575780B2

(12) United States Patent
Hamner et al.

(10) Patent No.: US 12,575,780 B2
(45) Date of Patent: Mar. 17, 2026

(54) SYSTEMS, DEVICES, AND METHOD FOR THE TREATMENT OF OSTEOARTHRITIS

(71) Applicant: Cala Health, Inc., San Mateo, CA (US)

(72) Inventors: Samuel Richard Hamner, San Francisco, CA (US); Kathryn H. Rosenbluth, San Francisco, CA (US); Scott Lee Delp, Stanford, CA (US); Daniel Lev Coleman, San Francisco, CA (US); Peter Bradley Shull, Atlanta, GA (US); Serena Hanying Wong, Palo Alto, CA (US)

(73) Assignee: Cala Health, Inc., San Mateo, CA (US)

( * ) Notice: Subject to any disclaimer, the term of this patent is extended or adjusted under 35 U.S.C. 154(b) by 0 days.

(21) Appl. No.: 18/231,049

(22) Filed: Aug. 7, 2023

(65) Prior Publication Data

US 2024/0197237 A1      Jun. 20, 2024

Related U.S. Application Data

(63) Continuation of application No. 15/748,616, filed as application No. PCT/US2016/045038 on Aug. 1, 2016, now abandoned.

(Continued)

(51) Int. Cl.
*A61B 5/11*          (2006.01)
*A61B 5/00*          (2006.01)
(Continued)

(52) U.S. Cl.
CPC ............ *A61B 5/112* (2013.01); *A61B 5/1121* (2013.01); *A61B 5/389* (2021.01); *A61B 5/4836* (2013.01);
(Continued)

(58) Field of Classification Search
CPC ....... A61B 5/389; A61B 5/4836; A61B 5/486; A61B 5/1038; A61B 5/6807;
(Continued)

(56) References Cited

U.S. PATENT DOCUMENTS

| | | | |
|---|---|---|---|
| 3,204,637 A | 9/1965 | Frank et al. | |
| 3,870,051 A | 3/1975 | Brindley | |

(Continued)

FOREIGN PATENT DOCUMENTS

| | | |
|---|---|---|
| AU | 2019/250222 | 6/2021 |
| AU | 2017211048 | 3/2022 |

(Continued)

OTHER PUBLICATIONS

U.S. Appl. No. 16/071,056, filed Jul. 18, 2018, Wong et al.

(Continued)

*Primary Examiner* — Amanda L Steinberg
(74) *Attorney, Agent, or Firm* — Knobbe, Martens, Olson & Bear, LLP

(57) ABSTRACT

The present disclosure describes devices, methods and systems for modifying or altering gait kinematics via sensory augmentation and/or modifying muscle activation patterns via augmented motor learning to slow the progression of and/or reduce the pain associated with knee OA, particularly during gait (e.g., walking, running, stair climbing, etc.). Sensors can be used to measure gait parameters and characteristics and muscle activation patterns. Stimulation can be provided to the individual in order to promote learning new gait kinematics and muscle activation patterns.

17 Claims, 13 Drawing Sheets

Related U.S. Application Data

(60) Provisional application No. 62/276,797, filed on Jan. 8, 2016, provisional application No. 62/199,965, filed on Jul. 31, 2015.

(51) Int. Cl.

| | | |
|---|---|---|
| *A61B 5/103* | (2006.01) | |
| *A61B 5/389* | (2021.01) | |
| *A61N 1/04* | (2006.01) | |
| *A61N 1/36* | (2006.01) | |

(52) U.S. Cl.
CPC .......... *A61B 5/486* (2013.01); *A61N 1/36003* (2013.01); *A61N 1/36031* (2017.08); *A61N 1/36034* (2017.08); *A61B 5/1038* (2013.01); *A61B 5/6807* (2013.01); *A61N 1/0456* (2013.01)

(58) Field of Classification Search
CPC ............ A61N 1/36031; A61N 1/36034; A61N 1/36003; A61N 1/0456
See application file for complete search history.

(56) References Cited

U.S. PATENT DOCUMENTS

| | | | |
|---|---|---|---|
| 4,103,808 A | 8/1978 | Hallman et al. |
| 4,233,986 A | 11/1980 | Tannenbaum |
| 4,300,575 A | 11/1981 | Wilson |
| 4,313,441 A | 2/1982 | Buffet |
| 4,458,696 A | 7/1984 | Larimore |
| 4,461,075 A | 7/1984 | Bailey |
| 4,539,996 A | 9/1985 | Engel |
| 4,569,351 A | 2/1986 | Tang |
| 4,582,049 A | 4/1986 | Ylvisaker |
| 4,729,377 A | 3/1988 | Granek et al. |
| 4,739,764 A | 4/1988 | Lue et al. |
| 4,763,659 A | 8/1988 | Dunseath, Jr. |
| 4,769,881 A | 9/1988 | Pedigo et al. |
| 4,771,779 A | 9/1988 | Tanagho et al. |
| 4,917,092 A | 4/1990 | Todd et al. |
| 4,981,146 A | 1/1991 | Bertolucci |
| 4,982,432 A | 1/1991 | Clark et al. |
| 4,996,987 A | 3/1991 | Petrofsky |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,395,398 A | 3/1995 | Rogozinski |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 5,961,542 A | 10/1999 | Agarwala |
| 6,016,449 A | 1/2000 | Fischell et al. |
| 6,076,018 A | 6/2000 | Sturman |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,364,841 B1 | 4/2002 | White et al. |
| 6,366,813 B1 | 4/2002 | DiLorenzo |
| 6,419,644 B1 | 7/2002 | White et al. |
| 6,445,955 B1 | 9/2002 | Michelson et al. |
| 6,449,512 B1 | 9/2002 | Boveja |
| 6,453,204 B1 | 9/2002 | Rhoads |
| 6,505,074 B2 | 1/2003 | Boveja et al. |
| 6,546,290 B1 | 4/2003 | Shloznikov |
| 6,564,103 B2 | 5/2003 | Fischer et al. |
| 6,572,555 B2 | 6/2003 | White et al. |
| 6,579,270 B2 | 6/2003 | Sussman et al. |
| 6,641,546 B2 | 11/2003 | White et al. |
| 6,652,449 B1 | 11/2003 | Gross et al. |
| 6,678,548 B1 | 1/2004 | Echauz et al. |
| 6,701,185 B2 | 3/2004 | Burnett et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,827,693 B2 | 12/2004 | White et al. |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,640,052 B2 | 12/2009 | Weinstock |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,801,585 B1 | 9/2010 | Weinstock |
| 7,857,771 B2 | 12/2010 | Alwan et al. |
| 7,899,527 B2 | 3/2011 | Yun et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,991,476 B2 | 8/2011 | Nachum |
| 7,996,088 B2 | 8/2011 | Marrosu et al. |
| 7,998,092 B2 | 8/2011 | Avni et al. |
| 8,000,796 B2 | 8/2011 | Tass et al. |
| 8,025,632 B2 | 9/2011 | Einarsson |
| 8,046,083 B2 | 10/2011 | Tegenthoff et al. |
| 8,064,988 B2 | 11/2011 | Weinstock |
| 8,075,499 B2 | 12/2011 | Nathan et al. |
| 8,086,318 B2 | 12/2011 | Strother et al. |
| 8,108,047 B2 | 1/2012 | Schumann |
| 8,121,694 B2 | 2/2012 | Molnar et al. |
| 8,145,316 B2 | 3/2012 | Deem et al. |
| 8,165,668 B2 | 4/2012 | Dacey, Jr. et al. |

(56) References Cited

U.S. PATENT DOCUMENTS

| | | | |
|---|---|---|---|
| 8,165,685 B1 | 4/2012 | Knutson et al. |
| 8,170,658 B2 | 5/2012 | Dacey, Jr. et al. |
| 8,175,718 B2 | 5/2012 | Wahlgren et al. |
| 8,187,209 B1 | 5/2012 | Guiffrida et al. |
| 8,190,249 B1 | 5/2012 | Gharieb et al. |
| 8,195,287 B2 | 6/2012 | Dacey, Jr. et al. |
| 8,209,036 B2 | 6/2012 | Nathan et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,265,763 B2 | 9/2012 | Fahey |
| 8,301,215 B2 | 10/2012 | Lee |
| 8,306,624 B2 | 11/2012 | Gerber et al. |
| 8,308,665 B2 | 11/2012 | Harry et al. |
| 8,313,443 B2 | 11/2012 | Tom |
| 8,326,398 B2 | 12/2012 | Weinstock |
| 8,326,432 B2 | 12/2012 | Kalisek |
| 8,343,026 B2 | 1/2013 | Gardiner et al. |
| 8,364,257 B2 | 1/2013 | Van Den Eerenbeemd et al. |
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,406,841 B2 | 3/2013 | Lin et al. |
| 8,409,116 B2 | 4/2013 | Wang et al. |
| 8,412,338 B2 | 4/2013 | Faltys |
| 8,414,507 B2 | 4/2013 | Asada |
| 8,417,351 B2 | 4/2013 | Kilger |
| 8,428,719 B2 | 4/2013 | Napadow |
| 8,430,805 B2 | 4/2013 | Burnett et al. |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,538,512 B1 | 9/2013 | Bibian et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| D709,874 S | 7/2014 | Aumiller et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,849,371 B2 | 9/2014 | Weinstock |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,079,029 B2 | 7/2015 | Weinstock |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,302,117 B2 | 4/2016 | De Vincentiis |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| D767,436 S | 9/2016 | Goodner et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,550,068 B2 | 1/2017 | Weinstock |
| 9,581,972 B1 | 2/2017 | Arrow et al. |
| 9,586,038 B1 | 3/2017 | Kosierkiewicz |
| 9,589,698 B2 | 3/2017 | Anhalt et al. |

(56) References Cited

U.S. PATENT DOCUMENTS

| | | | |
|---|---|---|---|
| 9,597,509 | B2 | 3/2017 | Hoffer et al. |
| 9,610,442 | B2 | 4/2017 | Yoo et al. |
| 9,610,459 | B2 | 4/2017 | Burnett et al. |
| 9,615,797 | B2 | 4/2017 | John |
| 9,630,004 | B2 | 4/2017 | Rajguru et al. |
| 9,649,486 | B2 | 5/2017 | Holzhacker |
| 9,656,070 | B2 | 5/2017 | Gozani et al. |
| 9,669,211 | B2 | 6/2017 | Wijting et al. |
| 9,675,800 | B2 | 6/2017 | Li et al. |
| 9,675,801 | B2 | 6/2017 | Kong et al. |
| 9,707,393 | B2 | 7/2017 | Hsueh et al. |
| 9,731,126 | B2 | 8/2017 | Ferree et al. |
| 9,757,584 | B2 | 9/2017 | Burnett |
| 9,782,584 | B2 | 10/2017 | Cartledge et al. |
| 9,802,041 | B2 | 10/2017 | Wong et al. |
| 9,826,921 | B2 | 11/2017 | Griffiths et al. |
| 9,861,283 | B1 | 1/2018 | Giuffrida |
| 9,877,679 | B1 | 1/2018 | Giuffrida |
| 9,877,680 | B1 | 1/2018 | Giuffrida et al. |
| 9,884,179 | B2 | 2/2018 | Bouton et al. |
| 9,924,899 | B2 | 3/2018 | Pracar et al. |
| 9,956,395 | B2 | 5/2018 | Bikson et al. |
| 9,974,478 | B1 * | 5/2018 | Brokaw ............... A61B 5/486 |
| 9,980,659 | B2 | 5/2018 | Sadeghian-Motahar et al. |
| 9,992,918 | B2 | 6/2018 | Watanabe et al. |
| 10,004,900 | B2 | 6/2018 | Kent et al. |
| 10,016,600 | B2 | 7/2018 | Creasey et al. |
| 10,022,545 | B1 | 7/2018 | Giuffrida |
| 10,028,695 | B2 | 7/2018 | Machado et al. |
| 10,045,740 | B2 | 8/2018 | John |
| 10,046,161 | B2 | 8/2018 | Biasiucci et al. |
| D828,351 | S | 9/2018 | Xie et al. |
| 10,076,656 | B2 | 9/2018 | Dar et al. |
| 10,080,885 | B2 | 9/2018 | Nathan et al. |
| 10,085,670 | B2 | 10/2018 | Crosson et al. |
| 10,112,040 | B2 | 10/2018 | Herb et al. |
| 10,118,035 | B2 | 11/2018 | Perez et al. |
| 10,130,809 | B2 | 11/2018 | Cartledge et al. |
| 10,130,810 | B2 | 11/2018 | Ferree et al. |
| 10,137,025 | B2 | 11/2018 | Fior et al. |
| 10,173,060 | B2 | 1/2019 | Wong et al. |
| 10,179,238 | B2 | 1/2019 | Wong et al. |
| 10,213,593 | B2 | 2/2019 | Kaplan et al. |
| 10,213,602 | B2 | 2/2019 | Ironi et al. |
| 10,232,174 | B2 | 3/2019 | Simon et al. |
| 10,252,053 | B2 | 4/2019 | Page et al. |
| 10,285,646 | B1 | 5/2019 | Grant et al. |
| 10,286,210 | B2 | 5/2019 | Yoo et al. |
| 10,293,159 | B2 | 5/2019 | Kong et al. |
| 10,335,594 | B2 | 7/2019 | Lin et al. |
| 10,335,595 | B2 | 7/2019 | Ferree et al. |
| 10,342,977 | B2 | 7/2019 | Raghunathan |
| 10,398,896 | B2 | 9/2019 | Lin et al. |
| 10,456,573 | B1 | 10/2019 | Feinstein et al. |
| 10,463,854 | B2 | 11/2019 | Perez |
| 10,499,848 | B2 | 12/2019 | Weinstock |
| 10,500,396 | B2 | 12/2019 | Tamaki et al. |
| 10,537,732 | B2 | 1/2020 | Nachum et al. |
| 10,549,093 | B2 | 2/2020 | Wong et al. |
| 10,556,107 | B2 | 2/2020 | Yoo et al. |
| 10,561,839 | B2 | 2/2020 | Wong et al. |
| 10,603,482 | B2 | 3/2020 | Hamner et al. |
| 10,610,114 | B2 | 4/2020 | Buckley et al. |
| 10,625,074 | B2 | 4/2020 | Rosenbluth et al. |
| 10,632,312 | B2 | 4/2020 | Ziv |
| 10,661,082 | B2 | 5/2020 | Kerselaers |
| 10,716,941 | B2 | 7/2020 | Yang et al. |
| 10,722,709 | B2 | 7/2020 | Yoo et al. |
| 10,765,856 | B2 | 9/2020 | Wong et al. |
| 10,773,079 | B2 | 9/2020 | Keller et al. |
| 10,780,269 | B2 | 9/2020 | Gozani et al. |
| 10,786,199 | B1 | 9/2020 | Giuffrida et al. |
| 10,786,669 | B2 | 9/2020 | Rajguru et al. |
| 10,814,130 | B2 | 10/2020 | Wong et al. |
| 10,814,131 | B2 | 10/2020 | Goldwasser et al. |
| D902,769 | S | 11/2020 | Riot et al. |
| 10,835,736 | B2 | 11/2020 | Horter et al. |
| 10,850,090 | B2 | 12/2020 | Rosenbluth et al. |
| 10,870,002 | B2 | 12/2020 | Wybo et al. |
| 10,905,879 | B2 | 2/2021 | Wong et al. |
| 10,918,853 | B2 | 2/2021 | Creasey et al. |
| 10,940,311 | B2 | 3/2021 | Gozani et al. |
| 10,945,879 | B2 | 3/2021 | Black et al. |
| 10,960,207 | B2 | 3/2021 | Wong et al. |
| D915,399 | S | 4/2021 | Chao et al. |
| 10,967,177 | B2 | 4/2021 | Lee |
| 11,026,835 | B2 | 6/2021 | Black et al. |
| 11,033,206 | B2 | 6/2021 | Roh |
| 11,033,731 | B2 | 6/2021 | Jeffery et al. |
| 11,033,736 | B2 | 6/2021 | Edgerton et al. |
| 11,058,867 | B2 | 7/2021 | Nathan et al. |
| 11,077,300 | B2 | 8/2021 | McBride |
| 11,077,301 | B2 | 8/2021 | Creasey et al. |
| 11,079,225 | B2 | 8/2021 | Ong et al. |
| 11,103,699 | B1 | 8/2021 | Oppenheim et al. |
| 11,141,586 | B2 | 10/2021 | Campean et al. |
| 11,141,587 | B2 | 10/2021 | Campean et al. |
| 11,160,971 | B2 | 11/2021 | Sharma et al. |
| 11,166,632 | B2 | 11/2021 | Grossman et al. |
| 11,197,999 | B2 | 12/2021 | Crosson |
| 11,213,681 | B2 | 1/2022 | Raghunathan |
| 11,224,742 | B2 | 1/2022 | Burnett |
| 11,247,040 | B2 | 2/2022 | Ferree et al. |
| 11,247,053 | B2 | 2/2022 | Rajguru et al. |
| 11,266,836 | B2 | 3/2022 | Charlesworth et al. |
| 11,278,724 | B2 | 3/2022 | Law et al. |
| 11,318,307 | B2 | 5/2022 | Kern et al. |
| 11,331,480 | B2 | 5/2022 | Hamner et al. |
| 11,338,120 | B2 | 5/2022 | Yun et al. |
| 11,338,128 | B2 | 5/2022 | Lawson et al. |
| 11,344,722 | B2 | 5/2022 | Wong et al. |
| 11,357,981 | B2 | 6/2022 | Moaddeb et al. |
| 11,383,087 | B1 | 7/2022 | Heldman et al. |
| 11,389,651 | B2 | 7/2022 | Tamaki et al. |
| 11,419,515 | B2 | 8/2022 | Crosson et al. |
| 11,420,052 | B2 | 8/2022 | Doskocil et al. |
| 11,424,755 | B2 | 8/2022 | Yang et al. |
| D962,929 | S | 9/2022 | He et al. |
| 11,484,710 | B2 | 11/2022 | Mantovani et al. |
| 11,504,530 | B2 | 11/2022 | Herr et al. |
| 11,517,753 | B2 | 12/2022 | Rhodes |
| 11,534,605 | B2 | 12/2022 | Bouton et al. |
| 11,547,316 | B2 | 1/2023 | Crosson et al. |
| 11,559,250 | B1 | 1/2023 | Giuffrida et al. |
| 11,590,348 | B2 | 2/2023 | Moaddeb et al. |
| 11,596,327 | B2 | 3/2023 | Griffiths et al. |
| 11,596,784 | B1 | 3/2023 | Hamner et al. |
| 11,596,791 | B2 | 3/2023 | Wong et al. |
| 11,596,792 | B2 | 3/2023 | Campean et al. |
| 11,623,078 | B2 | 4/2023 | Simon et al. |
| 11,628,300 | B2 | 4/2023 | Rajguru et al. |
| 11,642,513 | B2 | 5/2023 | Sharma et al. |
| 11,666,758 | B2 | 6/2023 | Crosson |
| 11,672,981 | B2 | 6/2023 | Jaasma et al. |
| 11,717,682 | B2 | 8/2023 | Gozani et al. |
| 11,744,482 | B1 | 9/2023 | Giuffrida et al. |
| 11,759,642 | B1 | 9/2023 | Heldman |
| 11,766,191 | B2 | 9/2023 | Sharma et al. |
| 11,833,352 | B2 | 12/2023 | Law et al. |
| 11,839,583 | B1 | 12/2023 | Carballo et al. |
| 11,839,762 | B2 | 12/2023 | Doskocil et al. |
| 11,844,943 | B2 | 12/2023 | Rajguru et al. |
| 11,857,778 | B2 | 1/2024 | Hamner et al. |
| 11,872,399 | B2 | 1/2024 | Raghunathan |
| 11,878,166 | B2 | 1/2024 | Colburn et al. |
| 11,890,468 | B1 | 2/2024 | Yu |
| 11,890,469 | B2 | 2/2024 | Moaddeb et al. |
| 11,896,824 | B2 | 2/2024 | Doskocil |
| 11,911,604 | B2 | 2/2024 | Sharma et al. |
| 11,911,605 | B2 | 2/2024 | Crosson et al. |
| 11,911,609 | B1 | 2/2024 | Heldman et al. |
| 11,918,806 | B2 | 3/2024 | Wong et al. |
| 11,975,190 | B2 | 5/2024 | Cho et al. |
| 11,986,317 | B1 | 5/2024 | Heldman et al. |

(56) References Cited

U.S. PATENT DOCUMENTS

| | | |
|---|---|---|
| 11,992,685 B2 | 5/2024 | Kassiri Bidhendi et al. |
| 12,029,287 B2 | 7/2024 | Ye et al. |
| 12,083,334 B2 | 9/2024 | Burnett |
| 12,109,413 B2 | 10/2024 | Wong et al. |
| 12,161,478 B1 | 12/2024 | Heldman et al. |
| 12,161,858 B2 | 12/2024 | Rosenbluth et al. |
| 12,161,865 B2 | 12/2024 | Hamner et al. |
| 12,179,012 B2 | 12/2024 | Simon et al. |
| 12,186,085 B2 | 1/2025 | Buckley et al. |
| 12,226,632 B2 | 2/2025 | Rajguru et al. |
| 12,237,121 B2 | 2/2025 | Ye et al. |
| 12,263,009 B1 | 4/2025 | Giuffrida et al. |
| 12,357,824 B2 | 7/2025 | Wong et al. |
| 2001/0020177 A1 | 9/2001 | Gruzdowich et al. |
| 2002/0055761 A1 | 5/2002 | Mann et al. |
| 2002/0138116 A1 | 9/2002 | Bertolucci |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0100932 A1 | 5/2003 | Ciaff |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0102819 A1 | 5/2004 | Zou et al. |
| 2004/0111129 A1 | 6/2004 | Gliner et al. |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0015042 A1 | 1/2005 | Sun et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171576 A1 | 8/2005 | Williams et al. |
| 2005/0171577 A1 | 8/2005 | Cohen et al. |
| 2005/0182454 A1 | 8/2005 | Gharib et al. |
| 2005/0222626 A1 | 10/2005 | DiLorenzo |
| 2005/0234309 A1 | 10/2005 | Klapper |
| 2005/0240241 A1 | 10/2005 | Yun et al. |
| 2006/0015153 A1 | 1/2006 | Gliner et al. |
| 2006/0047326 A1 | 3/2006 | Wheeler |
| 2006/0052726 A1 | 3/2006 | Weisz et al. |
| 2006/0074450 A1 | 4/2006 | Boveja et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0142874 A1 | 6/2007 | John |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0203534 A1 | 8/2007 | Tapper |
| 2007/0207193 A1 | 9/2007 | Zasler et al. |
| 2007/0249952 A1 | 10/2007 | Rubin et al. |
| 2007/0255319 A1 | 11/2007 | Greenberg et al. |
| 2007/0276217 A1 | 11/2007 | Brown et al. |
| 2007/0282228 A1 | 12/2007 | Einav et al. |
| 2007/0293917 A1 | 12/2007 | Thompson et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0030170 A1 | 2/2008 | Dacuay et al. |
| 2008/0033259 A1 | 2/2008 | Manto et al. |
| 2008/0033504 A1 | 2/2008 | Bertolucci |
| 2008/0033510 A1 | 2/2008 | Herregraven et al. |
| 2008/0051839 A1 | 2/2008 | Libbus et al. |
| 2008/0051845 A1 | 2/2008 | Mentelos |
| 2008/0058773 A1 | 3/2008 | John |
| 2008/0058871 A1 | 3/2008 | Libbus et al. |
| 2008/0058893 A1 | 3/2008 | Noujokat |
| 2008/0091256 A1 | 4/2008 | Libbus et al. |
| 2008/0097564 A1 | 4/2008 | Lathrop |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208282 A1 | 8/2008 | Gelfand et al. |
| 2008/0208288 A1 | 8/2008 | Podrazhansky et al. |
| 2008/0216593 A1 | 9/2008 | Jacobsen et al. |
| 2008/0243204 A1 | 10/2008 | Uthman et al. |
| 2008/0269593 A1 | 10/2008 | Weinstock |
| 2008/0288016 A1 | 11/2008 | Amurthur et al. |
| 2008/0300449 A1 | 12/2008 | Gerber et al. |
| 2008/0306325 A1 | 12/2008 | Burnett et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0082831 A1 | 3/2009 | Paul et al. |
| 2009/0099623 A1 | 4/2009 | Bentwich |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0249617 A1 | 10/2009 | Karicherla et al. |
| 2009/0270952 A1 | 10/2009 | Weinstock |
| 2009/0299435 A1 | 12/2009 | Gliner et al. |
| 2009/0312690 A1 | 12/2009 | Kim et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010572 A1 | 1/2010 | Skelton et al. |
| 2010/0036464 A1 | 2/2010 | Picciano |
| 2010/0057154 A1 | 3/2010 | Dietrich et al. |
| 2010/0059722 A1 | 3/2010 | Copp-Howland et al. |
| 2010/0076533 A1 | 3/2010 | Dar et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152623 A1* | 6/2010 | Williams ............ A61B 5/4082 |
| | | 600/595 |
| 2010/0152817 A1 | 6/2010 | Gillbe |
| 2010/0168501 A1 | 7/2010 | Burnett et al. |
| 2010/0168604 A1 | 7/2010 | Echauz |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0228180 A1 | 9/2010 | Jayes et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0004268 A1 | 1/2011 | Tcheng et al. |
| 2011/0009920 A1 | 1/2011 | Whitehurst et al. |
| 2011/0021899 A1 | 1/2011 | Arps et al. |

(56) References Cited

U.S. PATENT DOCUMENTS

| | | |
|---|---|---|
| 2011/0040204 A1 | 2/2011 | Ivorra et al. |
| 2011/0040288 A1 | 2/2011 | Eckstein et al. |
| 2011/0054358 A1 | 3/2011 | Kim et al. |
| 2011/0071590 A1 | 3/2011 | Mounaim et al. |
| 2011/0082524 A1 | 4/2011 | Thomas et al. |
| 2011/0098780 A1 | 4/2011 | Graupe et al. |
| 2011/0112605 A1 | 5/2011 | Fahey |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0196446 A1 | 8/2011 | Wu |
| 2011/0202107 A1 | 8/2011 | Sunagawa et al. |
| 2011/0208444 A1 | 8/2011 | Solinsky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0035674 A1 | 2/2012 | Weinstock |
| 2012/0035680 A1 | 2/2012 | Napadow |
| 2012/0046535 A1 | 2/2012 | Lin et al. |
| 2012/0050298 A1 | 3/2012 | Hoffman |
| 2012/0053491 A1 | 3/2012 | Nathan et al. |
| 2012/0059298 A1 | 3/2012 | Hoffman et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0098493 A1 | 4/2012 | Budike |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0203079 A1 | 8/2012 | McLaughlin |
| 2012/0211013 A1 | 8/2012 | Otis |
| 2012/0220812 A1 | 8/2012 | Mishelevich |
| 2012/0239112 A1 | 9/2012 | Muraoka |
| 2012/0245483 A1* | 9/2012 | Lundqvist ............... A61B 5/296 |
| | | 600/546 |
| 2012/0259255 A1 | 10/2012 | Tomlinson et al. |
| 2012/0277621 A1 | 11/2012 | Gerber et al. |
| 2012/0289869 A1 | 11/2012 | Tyler |
| 2012/0290036 A1 | 11/2012 | Karamanoglu et al. |
| 2012/0302821 A1 | 11/2012 | Burnett |
| 2012/0303080 A1 | 11/2012 | Ben-David et al. |
| 2012/0310298 A1 | 12/2012 | Besio et al. |
| 2012/0310299 A1 | 12/2012 | Norbert et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0035745 A1 | 2/2013 | Ahmed et al. |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0106684 A1 | 5/2013 | Weast et al. |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0178765 A1 | 7/2013 | Mishelevich |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0317565 A1 | 11/2013 | Weinstock |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046407 A1 | 2/2014 | Ben-Ezra et al. |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0081353 A1 | 3/2014 | Cook et al. |
| 2014/0094675 A1 | 4/2014 | Luna et al. |
| 2014/0094873 A1 | 4/2014 | Emborg et al. |
| 2014/0114117 A1 | 4/2014 | Naghavi et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1 | 5/2014 | Goldwasser et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0246628 A1 | 9/2014 | Anhalt et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0336731 A1 | 11/2014 | Weinstock |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0018926 A1 | 1/2015 | Frenkel et al. |
| 2015/0038886 A1 | 2/2015 | Snow |
| 2015/0042315 A1 | 2/2015 | Cen et al. |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148865 A1 | 5/2015 | Gozani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |

(56) References Cited

U.S. PATENT DOCUMENTS

| | | |
|---|---|---|
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0273234 A1 | 10/2015 | Weinstock |
| 2015/0277559 A1 | 10/2015 | Vescovi et al. |
| 2015/0297901 A1 | 10/2015 | Kockx |
| 2015/0321000 A1 | 11/2015 | Rosenbluth et al. |
| 2015/0335882 A1 | 11/2015 | Gross |
| 2015/0360030 A1 | 12/2015 | Cartledge et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0039239 A1 | 2/2016 | Ward et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0120432 A1 | 5/2016 | Sridhar et al. |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0144186 A1 | 5/2016 | Kaemmerer et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0262685 A1 | 9/2016 | Wagner et al. |
| 2016/0263376 A1 | 9/2016 | Yoo et al. |
| 2016/0279435 A1 | 9/2016 | Hyde et al. |
| 2016/0287879 A1 | 10/2016 | Denison et al. |
| 2016/0336722 A1 | 11/2016 | Taxter |
| 2016/0339239 A1 | 11/2016 | Yoo et al. |
| 2016/0361540 A9 | 12/2016 | Simon et al. |
| 2016/0375249 A1 | 12/2016 | Bonnet et al. |
| 2017/0014625 A1 | 1/2017 | Rosenbluth et al. |
| 2017/0027812 A1 | 2/2017 | Hyde et al. |
| 2017/0036025 A1 | 2/2017 | Sachs et al. |
| 2017/0042467 A1* | 2/2017 | Herr ........................ A61B 5/112 |
| 2017/0055880 A1* | 3/2017 | Agrawal .................. A43B 3/38 |
| 2017/0056238 A1 | 3/2017 | Yi et al. |
| 2017/0056643 A1 | 3/2017 | Herb et al. |
| 2017/0079597 A1 | 3/2017 | Horne |
| 2017/0080207 A1 | 3/2017 | Perez et al. |
| 2017/0087364 A1 | 3/2017 | Cartledge et al. |
| 2017/0095667 A1 | 4/2017 | Yakovlev et al. |
| 2017/0113045 A1 | 4/2017 | Baldassano et al. |
| 2017/0132067 A1 | 5/2017 | Singaravelu Vanaja et al. |
| 2017/0157398 A1 | 6/2017 | Wong et al. |
| 2017/0165485 A1 | 6/2017 | Sullivan et al. |
| 2017/0224991 A1 | 8/2017 | Wingeier et al. |
| 2017/0239415 A1 | 8/2017 | Hwang et al. |
| 2017/0246481 A1 | 8/2017 | Mishelevich |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0312513 A1 | 11/2017 | Hershey et al. |
| 2017/0361093 A1 | 12/2017 | Yoo et al. |
| 2017/0368329 A1 | 12/2017 | Tyler et al. |
| 2018/0001086 A1 | 1/2018 | Bartholomew et al. |
| 2018/0001088 A1 | 1/2018 | Tass |
| 2018/0021576 A1 | 1/2018 | Wong et al. |
| 2018/0028841 A1 | 2/2018 | Konofagou et al. |
| 2018/0036535 A1 | 2/2018 | Wong et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0116546 A1 | 5/2018 | Pastoor et al. |
| 2018/0132757 A1 | 5/2018 | Kong et al. |
| 2018/0140842 A1* | 5/2018 | Ó Laighin ............ A61B 5/112 |
| 2018/0168905 A1 | 6/2018 | Goodall et al. |
| 2018/0169400 A1 | 6/2018 | Wong et al. |
| 2018/0199841 A1 | 7/2018 | Yang et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2018/0345020 A1 | 12/2018 | Ironi et al. |
| 2019/0001117 A1 | 1/2019 | Ben-David et al. |
| 2019/0001129 A1 | 1/2019 | Rosenbluth et al. |
| 2019/0001139 A1 | 1/2019 | Mishra et al. |
| 2019/0126047 A1 | 5/2019 | Kassiri Bidhendi et al. |
| 2019/0134393 A1 | 5/2019 | Wong et al. |
| 2019/0143098 A1 | 5/2019 | Kaplan et al. |
| 2019/0143111 A1 | 5/2019 | Hamner et al. |
| 2019/0143113 A1 | 5/2019 | Wong et al. |
| 2019/0167976 A1 | 6/2019 | Byers et al. |
| 2019/0269914 A1 | 9/2019 | Moaddeb et al. |
| 2019/0298998 A1 | 10/2019 | Coleman et al. |
| 2019/0299008 A1 | 10/2019 | Rao |
| 2019/0321636 A1 | 10/2019 | Law et al. |
| 2019/0343462 A1 | 11/2019 | Grant et al. |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0069947 A1 | 3/2020 | Kent |
| 2020/0077943 A1 | 3/2020 | Weinstock |
| 2020/0093400 A1 | 3/2020 | Hamner et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0179687 A1 | 6/2020 | Wong et al. |
| 2020/0197707 A1 | 6/2020 | Covalin |
| 2020/0215324 A1 | 7/2020 | Mantovani et al. |
| 2020/0221975 A1* | 7/2020 | Basta ..................... A61B 5/112 |
| 2020/0254247 A1 | 8/2020 | Brezel et al. |
| 2020/0254251 A1 | 8/2020 | Wong et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |
| 2020/0324104 A1 | 10/2020 | Labuschagne et al. |
| 2020/0338348 A1 | 10/2020 | Honeycutt et al. |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0008369 A1 | 1/2021 | Crosson |
| 2021/0016079 A1 | 1/2021 | Ekelem et al. |
| 2021/0016089 A1 | 1/2021 | Crosson |
| 2021/0023376 A1 | 1/2021 | Hareland et al. |
| 2021/0031026 A1 | 2/2021 | Simon et al. |
| 2021/0031036 A1 | 2/2021 | Sharma et al. |
| 2021/0052883 A1 | 2/2021 | Wong et al. |
| 2021/0052897 A1 | 2/2021 | Bhadra et al. |
| 2021/0052900 A1 | 2/2021 | Pepin et al. |
| 2021/0060337 A1 | 3/2021 | Wybo et al. |
| 2021/0069507 A1 | 3/2021 | Gozani et al. |
| 2021/0085974 A1 | 3/2021 | Bouton et al. |
| 2021/0085976 A1 | 3/2021 | Heldman et al. |
| 2021/0100999 A1 | 4/2021 | Rosenbluth et al. |
| 2021/0101007 A1 | 4/2021 | Hamner et al. |
| 2021/0113834 A1 | 4/2021 | Wong et al. |
| 2021/0162212 A1 | 6/2021 | Kern et al. |
| 2021/0169684 A1 | 6/2021 | Black et al. |
| 2021/0187279 A1 | 6/2021 | Bouton et al. |

(56) References Cited

U.S. PATENT DOCUMENTS

| | | |
|---|---|---|
| 2021/0205619 A1 | 7/2021 | Wong et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |
| 2021/0252278 A1 | 8/2021 | Hamner et al. |
| 2021/0252279 A1 | 8/2021 | Kong et al. |
| 2021/0260379 A1 | 8/2021 | Charlesworth et al. |
| 2021/0266011 A1 | 8/2021 | Chen et al. |
| 2021/0283400 A1 | 9/2021 | Hamner et al. |
| 2021/0289814 A1 | 9/2021 | Hamner et al. |
| 2021/0299445 A1 | 9/2021 | Rajguru et al. |
| 2021/0308460 A1 | 10/2021 | Wong et al. |
| 2021/0330547 A1 | 10/2021 | Moaddeb et al. |
| 2021/0330974 A1 | 10/2021 | Wong et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0080196 A1 | 3/2022 | Crosson |
| 2022/0088373 A1 | 3/2022 | Burnett |
| 2022/0126095 A1 | 4/2022 | Rajguru et al. |
| 2022/0143391 A1 | 5/2022 | Vaishya et al. |
| 2022/0143392 A1 | 5/2022 | Labuschagne et al. |
| 2022/0143393 A1 | 5/2022 | Charlesworth et al. |
| 2022/0143402 A1 | 5/2022 | Oppenheim et al. |
| 2022/0203091 A1 | 6/2022 | Vysokov |
| 2022/0212007 A1 | 7/2022 | Rajguru et al. |
| 2022/0218991 A1 | 7/2022 | Moaddeb et al. |
| 2022/0220276 A1 | 7/2022 | Ziebell et al. |
| 2022/0233860 A1 | 7/2022 | Hamner et al. |
| 2022/0266011 A1 | 8/2022 | Hamner et al. |
| 2022/0266012 A1 | 8/2022 | Hamner et al. |
| 2022/0347461 A1 | 11/2022 | Campean et al. |
| 2022/0401721 A1 | 12/2022 | Jackson et al. |
| 2022/0409404 A1 | 12/2022 | Yang et al. |
| 2023/0009158 A1 | 1/2023 | Liberatore |
| 2023/0010696 A1 | 1/2023 | Pradeep |
| 2023/0062326 A1 | 3/2023 | Colachis et al. |
| 2023/0080790 A1 | 3/2023 | Crosson et al. |
| 2023/0086004 A1 | 3/2023 | Yang et al. |
| 2023/0110185 A1 | 4/2023 | Mantovani et al. |
| 2023/0191115 A1 | 6/2023 | Blum et al. |
| 2023/0191126 A1 | 6/2023 | Kent et al. |
| 2023/0200732 A1 | 6/2023 | Ye et al. |
| 2023/0201584 A1 | 6/2023 | Rajguru et al. |
| 2023/0207232 A1 | 6/2023 | Ye et al. |
| 2023/0218897 A1 | 7/2023 | Wang et al. |
| 2023/0233855 A1 | 7/2023 | Sunkeri et al. |
| 2023/0248962 A1 | 8/2023 | Zhang et al. |
| 2023/0256245 A1 | 8/2023 | Crosson |
| 2023/0277109 A1 | 9/2023 | Blum et al. |
| 2023/0277841 A1 | 9/2023 | Wang et al. |
| 2023/0285743 A1 | 9/2023 | Muccio |
| 2023/0293882 A1 | 9/2023 | Howe |
| 2023/0321430 A1 | 10/2023 | Ye et al. |
| 2023/0371846 A1 | 11/2023 | Sharma et al. |
| 2023/0381505 A1 | 11/2023 | Gozani et al. |
| 2024/0032819 A1 | 2/2024 | Zhao et al. |
| 2024/0058606 A1 | 2/2024 | Law et al. |
| 2024/0066286 A1 | 2/2024 | Yin et al. |
| 2024/0066287 A1 | 2/2024 | Siff |
| 2024/0090600 A1 | 3/2024 | Colachis et al. |
| 2024/0108239 A1 | 4/2024 | Crosson et al. |
| 2024/0122797 A1 | 4/2024 | Moaddeb et al. |
| 2024/0123230 A1 | 4/2024 | Raghunathan |
| 2024/0157142 A1 | 5/2024 | Yeniel et al. |
| 2024/0189594 A1 | 6/2024 | Hamner et al. |
| 2024/0226550 A1 | 7/2024 | Moaddeb et al. |
| 2024/0245388 A1 | 7/2024 | Plunger |
| 2024/0299734 A1 | 9/2024 | Wang et al. |
| 2024/0299735 A1 | 9/2024 | Wang et al. |
| 2024/0316339 A1 | 9/2024 | Keefer et al. |
| 2024/0325727 A1 | 10/2024 | Hamner et al. |
| 2024/0325728 A1 | 10/2024 | Schulte et al. |
| 2024/0335654 A1 | 10/2024 | Schulte et al. |
| 2024/0386553 A1 | 11/2024 | Akakin et al. |
| 2024/0406000 A1 | 12/2024 | Nguyen et al. |
| 2024/0428429 A1 | 12/2024 | Akakin et al. |
| 2025/0018185 A1 | 1/2025 | Ye et al. |
| 2025/0082924 A1 | 3/2025 | Simon et al. |
| 2025/0128058 A1 | 4/2025 | Hamner et al. |
| 2025/0135189 A1 | 5/2025 | Wong et al. |
| 2025/0135200 A1 | 5/2025 | Wong et al. |
| 2025/0161663 A1 | 5/2025 | Rosenbluth et al. |
| 2025/0161664 A1 | 5/2025 | Wong et al. |
| 2025/0161665 A1 | 5/2025 | Liberatore et al. |
| 2025/0161684 A1 | 5/2025 | Hamner et al. |
| 2025/0161685 A1 | 5/2025 | Hamner et al. |
| 2025/0170399 A1 | 5/2025 | Wong et al. |
| 2025/0195877 A1 | 6/2025 | Schulte et al. |
| 2025/0262430 A1 | 8/2025 | Ross et al. |

FOREIGN PATENT DOCUMENTS

| | | |
|---|---|---|
| CN | 1135722 | 11/1996 |
| CN | 1547483 | 11/2004 |
| CN | 1826154 | 8/2006 |
| CN | 101022849 | 8/2007 |
| CN | 101115524 | 1/2008 |
| CN | 101365373 | 2/2009 |
| CN | 101612043 | 12/2009 |
| CN | 101687093 | 3/2010 |
| CN | 101801453 | 8/2010 |
| CN | 102089031 | 6/2011 |
| CN | 102481394 | 5/2012 |
| CN | 102905757 | 1/2013 |
| CN | 202724457 | 2/2013 |
| CN | 103517732 | 1/2014 |
| CN | 103608069 | 2/2014 |
| CN | 103889503 | 6/2014 |
| CN | 104144729 | 11/2014 |
| CN | 104168951 | 11/2014 |
| CN | 104436431 | 3/2015 |
| CN | 104519960 | 4/2015 |
| CN | 104939815 | 9/2015 |
| CN | 105142714 A | 12/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 107949421 | 4/2018 |
| CN | 108697890 | 10/2018 |
| CN | 111358461 | 7/2020 |
| CN | 108348746 | 10/2021 |
| CN | 108778411 | 6/2022 |
| DE | 102008042373 | 4/2010 |
| DE | 102009004011 | 7/2010 |
| EP | 0000759 | 2/1979 |
| EP | 0801957 | 10/1997 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |
| EP | 2945691 | 11/2015 |
| EP | 3020448 | 5/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 3503960 | 3/2020 |

(56)            References Cited

FOREIGN PATENT DOCUMENTS

| | | |
|---|---|---|
| EP | 3650077 | 5/2020 |
| EP | 3352846 | 7/2020 |
| EP | 3493874 | 8/2020 |
| EP | 3409200 | 9/2020 |
| EP | 3427793 | 11/2020 |
| EP | 3758595 | 1/2021 |
| EP | 3641876 | 4/2021 |
| EP | 3352843 | 6/2021 |
| EP | 3679979 | 6/2021 |
| EP | 3841967 | 6/2021 |
| EP | 3402404 | 7/2021 |
| EP | 3562541 | 7/2021 |
| EP | 3675795 | 8/2021 |
| EP | 3100765 | 1/2022 |
| EP | 3487578 | 12/2022 |
| EP | 4108292 | 12/2022 |
| EP | 3784337 | 6/2023 |
| EP | 4233990 | 8/2023 |
| EP | 3541279 | 9/2023 |
| EP | 3463550 | 3/2024 |
| EP | 3565631 | 4/2024 |
| EP | 4356952 | 4/2024 |
| EP | 3842094 | 5/2024 |
| ES | 2222819 | 3/2006 |
| ES | 2272137 | 6/2008 |
| GB | 2496449 | 5/2013 |
| JP | 2010-527256 | 1/1900 |
| JP | 2002/200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008/018235 | 1/2008 |
| JP | 2009/34328 | 2/2009 |
| JP | 2009-512516 | 3/2009 |
| JP | 2009/529352 | 8/2009 |
| JP | 2010/506618 | 3/2010 |
| JP | 2010/512926 | 4/2010 |
| JP | 2010-246745 | 11/2010 |
| JP | 2012/005596 | 1/2012 |
| JP | 2012/055650 | 3/2012 |
| JP | 2012/217565 | 11/2012 |
| JP | 2013/017609 | 1/2013 |
| JP | 2013/094305 | 5/2013 |
| JP | 54-39921 | 3/2014 |
| JP | 2015-514460 | 5/2015 |
| JP | 2016-511651 | 4/2016 |
| JP | 2018-038597 | 3/2018 |
| KR | 20130104446 | 9/2013 |
| WO | WO 1987/01024 | 2/1987 |
| WO | WO1994/000187 | 1/1994 |
| WO | WO1994/017855 | 8/1994 |
| WO | WO 95/19804 | 7/1995 |
| WO | WO1996/032909 | 10/1996 |
| WO | WO 98/23326 | 6/1998 |
| WO | WO 98/40121 | 9/1998 |
| WO | WO1998/043700 | 10/1998 |
| WO | WO1999/019019 | 4/1999 |
| WO | WO2000/015293 | 3/2000 |
| WO | WO 2000/076436 | 12/2000 |
| WO | WO 01/03768 | 1/2001 |
| WO | WO 2001/087411 | 11/2001 |
| WO | WO2002/017987 | 3/2002 |
| WO | WO 2002034327 | 5/2002 |
| WO | WO 03/015866 | 2/2003 |
| WO | WO 2004/037344 | 5/2004 |
| WO | WO 2004/067087 | 8/2004 |
| WO | WO 2004/108209 | 12/2004 |
| WO | WO 2005/007029 | 5/2005 |
| WO | WO 2005/105201 | 11/2005 |
| WO | WO2005/122894 | 12/2005 |
| WO | WO 2006/021820 | 3/2006 |
| WO | WO 2006/044793 | 4/2006 |
| WO | WO 2006/092007 | 9/2006 |
| WO | WO 2006/102724 | 10/2006 |
| WO | WO 2007/056493 | 5/2007 |
| WO | WO 2007/092290 | 8/2007 |
| WO | WO2007/112092 | 10/2007 |
| WO | WO 2008/005478 | 1/2008 |
| WO | WO 2008/045598 | 4/2008 |
| WO | WO 2008/062395 | 5/2008 |
| WO | WO 2008/106174 | 9/2008 |
| WO | WO 2008/150591 | 12/2008 |
| WO | WO 2009/005797 | 1/2009 |
| WO | WO2009/153730 | 12/2009 |
| WO | WO 2010/014260 | 2/2010 |
| WO | WO 2010/031055 | 3/2010 |
| WO | WO2010/111321 | 9/2010 |
| WO | WO2010/141155 | 12/2010 |
| WO | WO 2011/106225 | 9/2011 |
| WO | WO2011/119224 | 9/2011 |
| WO | WO2011/144883 | 11/2011 |
| WO | WO 2011/149656 | 12/2011 |
| WO | WO2012/040243 | 3/2012 |
| WO | WO 2012/074794 | 6/2012 |
| WO | WO2013/071307 | 5/2013 |
| WO | WO2013/074809 | 5/2013 |
| WO | WO 2013/173727 | 11/2013 |
| WO | WO2014/043757 | 3/2014 |
| WO | WO2014/053041 | 4/2014 |
| WO | WO 2014/070999 | 5/2014 |
| WO | WO 2014/089549 | 6/2014 |
| WO | WO 2014/093964 | 6/2014 |
| WO | WO2014/113813 | 7/2014 |
| WO | WO2014/146082 | 9/2014 |
| WO | WO2014/151431 | 9/2014 |
| WO | WO2014/153201 | 9/2014 |
| WO | WO2014/207512 | 12/2014 |
| WO | WO2015/033152 | 3/2015 |
| WO | WO2015/039206 | 3/2015 |
| WO | WO2015/039244 | 3/2015 |
| WO | WO2015/042365 | 3/2015 |
| WO | WO2015/079319 | 6/2015 |
| WO | WO2015/095880 | 6/2015 |
| WO | WO2015/128090 | 9/2015 |
| WO | WO 2015/138981 | 9/2015 |
| WO | WO2015/164706 | 10/2015 |
| WO | WO2015/187712 | 12/2015 |
| WO | WO2016/007093 | 1/2016 |
| WO | WO2016/019250 | 2/2016 |
| WO | WO 2016/032929 | 3/2016 |
| WO | WO2016/094728 | 6/2016 |
| WO | WO2016/102958 | 6/2016 |
| WO | WO2016/110804 | 7/2016 |
| WO | WO2016/128985 | 8/2016 |
| WO | WO2016/149751 | 9/2016 |
| WO | WO2016/166281 | 10/2016 |
| WO | WO 2016/176668 | 11/2016 |
| WO | WO2016/179407 | 11/2016 |
| WO | WO2016/189422 | 12/2016 |
| WO | WO2016/195587 | 12/2016 |
| WO | WO2016/201366 | 12/2016 |
| WO | WO2017/004021 | 1/2017 |
| WO | WO2017/010930 | 1/2017 |
| WO | WO2017/023864 | 2/2017 |
| WO | WO 2017/044904 | 3/2017 |
| WO | WO2017/053847 | 3/2017 |
| WO | WO2017/062994 | 4/2017 |
| WO | WO2017/086798 | 5/2017 |
| WO | WO2017/088573 | 6/2017 |
| WO | WO2017/132067 | 8/2017 |
| WO | WO2017/199026 | 11/2017 |
| WO | WO2017/208167 | 12/2017 |
| WO | WO2017/209673 | 12/2017 |
| WO | WO2017/210729 | 12/2017 |
| WO | WO2017/221037 | 12/2017 |
| WO | WO2018/009680 | 1/2018 |
| WO | WO2018/028170 | 2/2018 |
| WO | WO2018/028220 | 2/2018 |
| WO | WO2018/028221 | 2/2018 |
| WO | WO2018/039458 | 3/2018 |
| WO | WO2018/093765 | 5/2018 |
| WO | WO 2018/106839 | 6/2018 |
| WO | WO2018/112164 | 6/2018 |

(56) References Cited

FOREIGN PATENT DOCUMENTS

| WO | WO 2018119220 | 6/2018 |
| WO | WO2018/187241 | 10/2018 |
| WO | WO2019/005774 | 1/2019 |
| WO | WO2019/014250 | 1/2019 |
| WO | WO2019/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO2020/086726 | 4/2020 |
| WO | WO 2020/131857 | 6/2020 |
| WO | WO 2020/185601 | 9/2020 |
| WO | WO 2020/252406 | 12/2020 |
| WO | WO 2021/005584 | 1/2021 |
| WO | WO 2021/055716 | 3/2021 |
| WO | WO 2021/062345 | 4/2021 |
| WO | WO 2021/092533 | 5/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | WO 2022/090834 | 5/2022 |
| WO | WO 2022/187318 | 9/2022 |
| WO | WO 2022/187486 | 9/2022 |
| WO | WO 2022/221858 | 10/2022 |
| WO | WO 2022/235607 | 11/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |
| WO | WO 2023/129722 | 7/2023 |
| WO | WO 2023/156391 | 8/2023 |
| WO | WO 2023/163300 | 8/2023 |
| WO | WO 2023/168016 | 9/2023 |
| WO | WO 2023/191236 | 10/2023 |
| WO | WO 2023/192519 | 10/2023 |
| WO | WO 2023/196578 | 10/2023 |
| WO | WO 2023/215558 | 11/2023 |
| WO | WO 2023/222911 | 11/2023 |
| WO | WO 2024/059136 | 3/2024 |
| WO | WO 2024/059140 | 3/2024 |
| WO | WO 2024/059141 | 3/2024 |
| WO | WO 2024/059643 | 3/2024 |
| WO | WO 2024/059651 | 3/2024 |
| WO | WO 2024/059663 | 3/2024 |
| WO | WO 2024/083685 | 4/2024 |
| WO | WO 2024/119042 | 6/2024 |
| WO | WO 2024/155527 | 7/2024 |
| WO | WO 2024/182256 | 9/2024 |
| WO | WO 2024/206883 | 10/2024 |
| WO | WO 2024/238988 | 11/2024 |
| WO | WO 2025/038622 | 2/2025 |
| WO | WO 2025/049694 | 3/2025 |
| WO | WO 2025/128510 | 6/2025 |
| WO | WO 2025/128825 | 6/2025 |
| WO | WO 2025/151398 | 7/2025 |
| WO | WO 2025/151439 | 7/2025 |
| WO | WO 2025/155529 | 7/2025 |

OTHER PUBLICATIONS

U.S. Appl. No. 16/327,780, filed Feb. 22, 2019, Hamner et al.
U.S. Appl. No. 16/780,758, filed Feb. 3, 2020, Wong et al.
U.S. Appl. No. 16/833,388, filed Mar. 27, 2020, Hamner et al.
U.S. Appl. No. 16/962,810, filed Jul. 16, 2020, Hamner et al.
U.S. Appl. No. 16/993,085, filed Aug. 13, 2020, Balbaky, et al.
U.S. Appl. No. 17/013,396, filed Sep. 4, 2020, Wong et al.
U.S. Appl. No. 17/052,483, filed Nov. 2, 2020, Liberatore et al.
U.S. Appl. No. 17/061,231, filed Oct. 1, 2020, Yu.

U.S. Appl. No. 17/080,544, filed Oct. 26, 2020, Wong et al.
Aparatis; Clinical neurophysiology in movement disorders. Handb Clin Neurol; 111; Pediatric Neurology Pt. 1; pp. 87-92; Apr. 2013.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation .; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brazilian Preliminary Office Action dated Jul. 7, 2020 in Brazilian Industrial Property Journal No. 2583 for BR112016025203-9.
Brazilian Preliminary Office Action dated Jun. 30, 2020 in Brazilian Industrial Property Journal No. 2582 for BR1120150170420 in 4 pgs.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006 (part 1, Title to p. 142).
Buschbacher et al.; Manual of nerve conduction series; 2nd edition; Demos Medical Publishing, LLC; 2006 (part 2, p. 143 to 299).
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.

(56)                  References Cited

OTHER PUBLICATIONS

Clair et al.; Postactivation depression and recovery of reflex trans-mission during repetitive electrical stimulation of the human tibial nerve, Journal of Neurophysiology; vol. 106, No. 1; pp. 184-192; Jul. 2011.

Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.

Constandinou et al.; A Partial-Current-Steering Biphasic Stimula-tion Driver for Vestibular Prostheses; IEEE Trans on Biomedical Circuits and Systems; 2(2); pp. 106-113; Jun. 2008.

Daneault et al.; Using a smart phone as a standalone platform for detection and monitoring of pathological tremors; Frontiers in Human Neuroscience; vol. 6, article 357; 12 pgs.; Jan. 2012.

Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filing date and any foreign priority date) 1998.

Di Giovangiulio et al.; The Neuromodulation of the intestinal immune system and its relevance in inflammatory bowel disease; Fronteir's in Immunology; vol. 6; Article 590; Nov. 2015.

Dideriksen et al.; EMG-based characterization of pathological tremor using the iterated Hilbert transform; IEEE transactions on Bio-medical Engineering; 58(10); pp. 2911-2921; Oct. 2011.

Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.

Doucet et al.; Neuromuscular electrical stimulation for skeletal muscle function; The Yale Journal of Biology and Medicine; 85(2); pp. 201-215; Jun. 2012.

European Office Action dated Jun. 5, 2020 in European Application No. 16849785.7 in 4 pgs.

Extended European Search Report dated Feb. 4, 2019 in European Application No. 16833688.1 in 10 pages.

Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).

Fuentes et al.; Spinal cord stimulation restores locomotion in animal models of Parkinson's disease; Science; 323; pp. 1578-1582; Mar. 2009.

Gallego et al.; A neuroprosthesis for tremor management through the control of muscle co-contraction; Journal of Neuroengineering and Rehabilitation; vol. 10; 36; (13 pgs); Apr. 2013.

Gallego et al.; Real-time estimation of pathological tremor param-eters from gyroscope data.; Sensors; 10(3); pp. 2129-2149; Mar. 2010.

Gallego et al.; A soft wearable robot for tremor assessment and suppression; 2011 IEEE International Conference on Robotics and Automation; Shanghai International Conference Center; pp. 2249-2254; May 9-13, 2011.

Gao; Analysis of amplitude and frequency variations of essential and Parkinsonian tremors; Medical & Biological Engineering & Computing; 42(3); pp. 345-349; May 2004.

Garcia et al.; Modulation of brainstem activity and connectivity by respiratory-gated auricular vagal afferent nerve stimulation in migraine patients; Pain; International Association for the Study of Pain; 2017.

Garcia-Rill, E., et al. "Arousal, motor control, and Parkinson's disease." Translational neuroscience 6.1 pp. 198-207 (2015).

Giuffridda et al.; Clinically deployable Kinesia technology for automated tremor assessment.; Movement Disorders; 24(5); pp. 723-730; Apr. 2009.

Gracanin et al.; Optimal stimulus parameters for minimum pain in the chronic stimulatin of innervated muscle; Archives of Physical Medicine and Rehabilitation; 56(6); pp. 243-249; Jun. 1975.

Haeri et al.; Modeling the Parkinson's tremor and its treatments; Journal of Theorectical Biology; 236(3); pp. 311-322; Oct. 2005.

Halon EN et al.; Contribution of cutaneous and muscle afferent fibres to cortical SEPs following median and radial nerve stimula-tion in man; Electroenceph. Clin. Neurophysiol.; 71(5); pp. 331-335; Sep.-Oct. 1988.

Hao et al.; Effects of electrical stimulation of cutaneous afferents on corticospinal transmission of tremor signals in patients with Par-kinson's disease; 6th International Conference on Neural Engineer-ing; San Diego, CA; pp. 355-358; Nov. 2013.

Hauptmann et al.; External trial deep brain stimulation device for the application of desynchronizing stimulation techniques; Journal of Neural Engineering; 6; 12 pgs.; Oct. 2009.

Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.

Henry Dreyfuss Associates; The Measure of Man and Woman: Human Factors in Design (Revised Edition); John Wiley & Sons, New York; pp. 10-11 and 22-25; Dec. 2001.

Hernan, Miguel, et al. "Alcohol Consumption and the Incidence of Parkinson's Disease." May 15, 2003. Annals of Neurology. vol. 54. pp. 170-175.

Hua et al.; Posture-related oscillations in human cerebellar thalamus in essential tremor are enabled by voluntary motor circuits; J Neurophysiol; 93(1); pp. 117-127; Jan. 2005.

Huang, et al.; Theta burst stimulation report of the human motor cortex; Neuron, vol. 45, 201-206, Jan. 20, 2005.

Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.

Hubeaux, Katelyne, et al. "Evidence for autonomic nervous system dysfunction in females with idiopathic overactive bladder syn-drome." Neurourology and urodynamics 30.8 (2011): 1467-1472.

Inoue, Masahiro, Katsuaki Suganuma, and Hiroshi Ishiguro. "Stretch-able human interface using a conductive silicone elastomer con-taining silver fillers." Consumer Electronics, 2009. ISCE'09. IEEE 13th International Symposium on. IEEE, 2009.

Israel Preliminary Office Action dated Jan. 27, 2020 for Application No. 264116 in 4 pgs.

Jacks et al.; Instability in human forearm movements studied with feed-back-controlled electrical stimulation of muscles; Journal of Physiology; 402; pp. 443-461; Aug. 1988.

Jobges et al.; Vibratory proprioceptive stimulation affects Parkin-sonian tremor; Parkinsonism & Related Disorders; 8(3); pp. 171-176; Jan. 2002.

Joundi et al.; Rapid tremor frequency assessment with the iPhone accelerometer .; Parkinsonism & Related Disorders; 17(4); pp. 288-290; May 2011.

Kim et al.: Adaptive control of movement for neuromuscular stimulation-assisted therapy in a rodent model; IEEE Trans on Biomedical Engineering,; 56(2); pp. 452-461; Feb. 2009.

Krauss et al.; Chronic spinal cord stimulation in medically intrac-table orthostatic tremor; J Neurol Neurosurg Psychiatry; 77(9); pp. 1013-1016; Sep. 2006.

Kuhn et al.; Array electrode design for transcutaneous electrical stimulation a simulation study; Medical Engineering & Physics; 31 (8); pp. 945-951; Oct. 2009.

Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.

Kunz, Patrik, et al. "5 kHz transcranial alternating current stimu-lation: lack of cortical excitability changes when grouped in a theta burst pattern." Frontiers in Human Neuroscience 10 (2016): 683.

Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.

Laroy et al.; The sensory innervation pattern of the fingers; J. Neurol .; 245 (5); pp. 294-298; May 1998.

Lee et al.; Resetting of tremor by mechanical perturbations: A comparison of essential tremor and parkinsonian tremor; Annals of Nuerology; 10(6); pp. 523-531; Dec. 1981.

(56) References Cited

OTHER PUBLICATIONS

Legon et al.; Pulsed ultrasound differentially stimulates somatosensory circuits in humans as indicated by EEG and fMRI; PLoS ONE; 7(12); e51177; 14 pgs.; Dec. 2012.

Liao, Wen-Chien, et al. "A noninvasive evaluation of autonomic nervous system dysfunction in women with an overactive bladder." International Journal of Gynecology & Obstetrics 110.1 (2010): 12-17.

Lourenco et al.; Effects produced in human arm and forearm motoneurones after electrical stimulation of ulnar and median nerves at wrist level; Experimental Brain Research; 178(2); pp. 267-284; Apr. 2007.

Malek et al.; The utility of electromyography and mechanomyography for assessing neuromuscular function: a noninvasive approach; Phys Med Rehabil in N Am; 23(1); pp. 23-32; Feb. 2012.

Mamorita et al.; Development of a system for measurement and analysis of tremor using a three-axis accelerometer; Methods Inf Med; 48(6); pp. 589-594; epub Nov. 2009.

Maneski et al.; Electrical Stimulation for suppression of pathological tremor; Med Biol Eng Comput; 49(10); pp. 1187-1193; Oct. 2011.

Marsden et al.; Coherence between cerebellar thalamus, cortex and muscle in man; Brain; 123; pp. 1459-1470; Jul. 2000.

Marshall, Ryan, et al. "Bioelectrical stimulation for the reduction of inflammation in inflammatory bowel disease." Clinical Medicine Insights: Gastroenterology 8 (2015): CGast-S31779.

McAuley et al.; Physiological and pathological tremors and rhythmic central motor control; Brain; 123(Pt 8); pp. 1545-1567; Aug. 2000.

McIntyre et al.; Finite element analysis of current-density and electric field generated by metal microelectrodes; Annals of Biomedical Engineering; 29(3); pp. 227-235; Mar. 2001.

Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.

Mehnert, Ulrich, et al. "Heart rate variability: an objective measure of autonomic activity and bladder sensations during urodynamics." Neurourology and urodynamics 28.4 (2009): 313-319.

Miguel et al.; Alcohol consumption and the incidence of Parkinson's disease; Ann. Neurol.; 54(2); pp. 170-175; May 15, 2003.

Miller et al.; Multiplexed microneedle-based biosensor array for characterization of metabolic acidosis; Talanta; 88; pp. 739-742; Jan. 2012 (author manuscript; 13 pgs.).

Miller et al.; Neurostimulation in the treatment of primary headaches; Pract Neurol; Apr. 11, 2016;16:pp. 362-375.

Milne et al.; Habituation to repeated in painful and non-painful cutaneous stimuli: A quantitative psychophysical study; Experimental Brain Research; 87(2); pp. 438-444; Nov. 1991.

Mommaerts et al.; Excitation and nerve conduction; in Comprehensive Human Physiology; Springer Berlin Heidelberg; Chap. 13; pp. 283-294; Mar. 1996.

Mones et al.; The response of the tremor of patients with Parkinsonism to peripheral nerve stimulation; J Neurology, Neurosurgery, and Psychiatry; 32(6); pp. 512-518; Dec. 1969.

Morgante et al.: How many parkinsonian patients are suitable candidates for deep brain stimulation of subthalamic nucleus ?; Results of a Questionnaire, Partkinsonism Relat Disord; 13; pp. 528-531; Dec. 2007.

Munhoz et al.; Acute effect of transcutaneous electrical nerve stimulation on tremor; Movement Disorders; 18(2); pp. 191-194; Feb. 2003.

Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.

Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.

PCT Search Report and Written Opinion in PCT Application No. PCT/US2016/045038 mailed Nov. 15, 2016 in 16 pages.

Perez et al.; Patterned Sensory Stimulation Induces Plasticity in Reciprocal Ia Inhibition in Humans; The Journal of Neuroscience; 23(6); pp. 2014-2018; Mar. 2003.

Perlmutter et al.; Deep brain stimulation; Ann Rev Neurosci; 29; pp. 229-257; Jul. 2006.

Popović-Bijelić, Ana, et al. "Multi-field surface electrode for selective electrical stimulation." Artificial organs 29.6 (2005): 448-452.

Prochazka et al.; Attenuation of pathological tremors by functional electrical stimulation I: Method; Annals of Biomedical Engineering; 20(2); pp. 205-224; Mar. 1992.

Pulliam et al.; Continuous in-home monitoring of essential tremor; Parkinsonism Relat Disord; 20(1); pp. 37-40; Jan. 2014.

Quattrini et al.; Understanding the impact of painful diabetic neuropathy; Diabetes/Metabolism Research and Reviews; 19, Suppl. 1; pp. S2-S8; Jan.-Feb. 2003.

Rocon et al.; Design and validation of a rehabilitation robotic exoskeleton for tremor assessment and suppression; IEEE Trans Neural Sys and Rehab Eng.; 15(3); pp. 367-378; Sep. 2007.

Silverstone et al.; Non-Invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.

Singer et al.; The effect of EMG triggered electrical stimulation plus task practice on arm function in chronic stroke patients with moderate-severe arm deficits; Restor Neurol Neurosci; 31(6); pp. 681-691; Oct. 2013.

Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.

Takanashi et al.; A functional MRI study of somatotopic representation of somatosensory stimulation in the cerebellum; Neuroradiology; 45(3); pp. 149-152; Mar. 2003.

Tass et al.; Coordinated reset has sustained aftereffects in Parkinsonian monkeys; Ann Neurol; 72(5); pp. 816-820; Nov. 2012.

Tass et al.; Counteracting tinnitus by acoustic coordinated reset neuromodulation; Restorative neurology and Neuroscience; 30(2); pp. 137-159; Apr. 2012.

Tass; A Model of desynchronizing deep brain stimulation with a demand-controlled coordinated reset of neural subpopulations; Bioi Cybern; 89(2); pp. 81-88; Aug. 2003.

Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.

Toloso et al.; Essential tremor: treatment with propranolol; Neurology; 25(11); pp. 1041; Nov. 1975.

Tracey; The inflammatory reflex; Nature; vol. 420; pp. 853-859; 19/26 Dec. 2002.

Treager; Interpretation of skin impedance measurements; Nature; 205; pp. 600-601; Feb. 1965.

Valente; Novel methods and circuits for field shaping in deep brain stimulation; Doctoral thesis, UCL (University College London); 222 pgs.; 2011.

Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.

Von Lewinski et al.; Efficacy of EMG-triggered electrical arm stimulation in chronic hemiparetic stroke patients; Restor Neurol Neurosci; 27(3); pp. 189-197; Jun. 2009.

Wardman et al.; Subcortical, and cerebellar activation evoked by selective stimulation of muscle and cataneous afferents: an fMRI study; Physiol. Rep.; 2(4); pp. 1-16; Apr. 2014.

Wiestler et al.; Integration of sensory and motor representations of single fingers in the human; J. Neurophysiol.; 105(6); pp. 3042-3053; Jun. 2011.

Woldag et al.; Evidence-based physiotherapeutic concepts for improving arm and hand function in stroke patients R A review; J Neurol; 249(5); pp. 518-528; May 2002.

(56)        References Cited

OTHER PUBLICATIONS

Woolf et al.; Peripheral nerve injury triggers central sprouting of myelinated afferents; Nature; 355(6355); pp. 75-78; Jan. 1992.

Yarnitsky et al.; Nonpainful remote electrical stimulation alleviates episodic migraine pain; Neurology 88; pp. 1250-1255; Mar. 28, 2017.

Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.

Yilmaz, Ozlem O., et al. "Efficacy of EMG-biofeedback in knee osteoarthritis." Rheumatology international 30.7 (2010): 887-892.

Zhang et al.; Neural oscillator based control for pathological tremor suppression via functional electrical stimulation; Control Engineering Practice; 19(1); pp. 74-88; Jan. 2011.

Zorba et al.; Overactive bladder and the pons; Rize University, Medical Faculty, Department of Urology; 123-124; Undated.

Zwarts et al.; Multichannel surface EMG: basic aspects and clinical utility; Muscle Nerve; 28(1); pp. 1-17; Jul. 2003.

V. Krishnamoorthy et al., "Gait Training After Stroke: A Pilot Study Combining a Gravity-Balanced Orthosis, Functional Electrical Stimulation, and Visual Feedback", Journal of Neurologic Physical Therapy, vol. 32, No. 4, pp. 192-202, 2008. Available: 10.1097/npt.0b013e31818e8fc2 (Year: 2008).

Sigrist, R., Rauter, G., Riener, R. and Wolf, P., 2012. Augmented visual, auditory, haptic, and multimodal feedback in motor learning: A review. Psychonomic Bulletin & Review, 20(1), pp. 21-53 (Year: 2012).

Solomonow, Met al. "Studies Toward Spasticity Suppression With High Frequency Electrical Stimulation". Orthopedics, vol. 7, No. 8, 1984, pp. 1284-1288. Slack, Inc., https://doi.org/10.3928/0147-7447-19840801-11 (Year: 1998).

Fiorentino, M., A. E. Uva, and M. M. Foglia. "Self calibrating wearable active running asymmetry measurement and correction." Journal of Control Engineering and Applied Informatics 13.2 (2011): 3-8. (Year: 2011).

Amarenco et al. "Urondynamic Effect of Acute Transcutaneous Posterior Tibial Nerve Stimulation in Overactive Bladder" Journal of Urology vol. 169, 2210-2215 (Jun. 2003).

Barath et al., 2020, Brain metabolic changes with longitudinal transcutaneous afferent patterned stimulation in essential tremor subjects, Tremor and Other Hyperkinetic Movements, 10(1):52, pp. 1-10.

Brillman et al., 2022, Real-world evidence of transcutaneous afferent patterned stimulation for essential tremor, Tremor and Other Hyperkinetic Movements, 12(1):27, pp. 1-11.

Ferreira et al., 2019, MDS evidence-based review of treatments for essential tremor, Movement Disorders, 34(7):950-958.

Fred E. Govier, et al., "Percutaneous Afferent Neuromodulation for the Refractory Overactive Bladder: Results of a Multicenter Study," 165 J. Urology 1193-1198 (Apr. 2001).

Gupta et al., 2021, Exploring essential tremor: results from a large online survey, Clinical Parkinsonism & Related Disorders, 5:100101, 4 pp.

H.C. Klingler, et al., "Use of Peripheral Neuromodulation of the S3 Region for Treatment of Detrusor Overactivity: A Urodynamicbased Study," Urology 56:766-771, 2000.

Haubenberger et al., 2018, Essential Tremor, The New England Journal of Medicine, 378:1802-1810 and Supplementary Appendix.

Hellwig et al., Feb. 17, 2001, Tremor-correlated cortical activity in essential tremor, The Lancet, 357:519-523.

Hernandez-Martin et al., 2021, High-fidelity transmission of high-frequency burst stimuli from peripheral nerve to thalamic nuclei in children with dystonia, Scientific Reports, 11:8498, 9 pp.

Isaacson et al., 2020, Prospective home-use study on non-invasive neuromodulation therapy for essential tremor, Tremor and Other Hyperkinetic Movements, 10(1):29, pp. 1-16.

Knutson et al., Neuromuscular Electrical Stimulation for Motor Restoration in Hemiplegia. Phys Med Rehabil Clin N A,. Nov. 2015; 26(4): 729-745. Published online Aug. 14, 2015. Doi: 10.1016/j.pmr.2015.06.002.

Lin et al., 2018, Noninvasive neuromodulation inessential tremor demonstrates relief in a sham-controlled pilot trial, Movement Disorders, 33(7):1182-1183.

Llinas et al., Dec. 21, 1999, Thalamocortical dysrhythmia: a neurological and neuropsychiatric syndrome characterized by magnetoencephalography, PNAS, 96(26):15222-15227.

Michael R. Van Balken, et al., "Posterior Tibial Nerve Stimulation as Neuromodulative Treatment of Lower Urinary Track Dysfunction," 166 J. Urology 914-918 (Sep. 2001).

Pahwa et al., 2018, An acute randomized controlled trial of noninvasive peripheral nerve stimulation in essential tremor, Neuromodulation, 22:537-545.

Peng et al., 2015, Flexible dry electrode based on carbon nanotube/polymer hybrid micropillars for biopotential recording, Sensor and Actuatora A: Physical, 235:48-65.

Perez-Reyes, Jan. 2003, Molecular physiology of low-voltage-activated T-type calcium channels, Physiol. Rev. 83:117-161.

Popovi Maneski et al.; Electrical stimulation for the suppression of pathological tremor; Medical & Biological Engineering & Computing; 49(10); pp. 1187-1193; Oct. 2011.

Wallerberger, Apr. 4, 2019, Efficient Estimation of Autocorrelation Spectra, ArXiv.org, https://arxiv.org/abs/1810.05079.

Cala Trio Health Care Professional Guide (Jul. 2020).

Cala Trio Health Care Professional Guide (Nov. 2019).

Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).

Javidan, et al, Attenuation of Pathological Tremors by Functional Electrical Stimulation II: Clinical Evaluation, 20 Annals of Biomedical Engineering 225 (1992).

Aemed, Inc., 510(k) Summary, StimPad™ TENS System, Dec. 6, 2007.

Antal et al., Anodal Transcranial Direct Current Stimulation of the Motor Cortex Ameliorates Chronic Pain and Reduces Short Intracortical Inhibition, Journal of Pain and Symptom Management, vol. 39, No. 5, pp. 890-903, May 2010.

Cala kIQ, calahealth.com, [online], [site visited Mar. 7, 2025], Available from internet URL: https://calahealth.com/ (Year: 2025).

De Santana, et al., Effectiveness of Transcutaneous Electrical Nerve Stimulation for Treatment of Hyperalgesia and Pain, Curr Rheumatol Rep.; 10(6): 492-499, Dec. 2008.

Dewey, et al., A Pilot Study of Ai-Controled Transcutaneous Peripheral Nerve Stimulation for Essential Tremor, Tremor and Other Hyperkinetic Movements, 2025; 15(1):10, pp. 1-9.

Encore Medical, L.P., Intelect Transport 2 Channel Electrotherapy User Manual, 2005.

Falco et al., Cross Talk: A New Method for Peripheral Nerve Stimulation. An Observational Report with Cadaveric Verification, Pain Physician, 12:965-983, 2009.

Fowler et al., The conduction velocities of peripheral nerve fibres conveying sensations of warming and cooling, Journal of Neurology, Neurosurgery and Psychiatry Sep. 1988;51(9):1164-70.

Griffin et al., Efficacy of High Voltage Pulsed Current for Healing of Pressure Ulcers in Patents with Spinal Cord Injury, Physical Therapy, vol. 71, No. 6, Jun. 1991, pp. 433-442.

Johnson, Factors Influencing The Analgesic Effects and Clinical Efficacy of Transcutaneous Electrical Nerve Stimulation (TENS), Newcastle University, Jul. 1991.

Jones et al., Transcutaneous electronical nerve stimulation, Continuing Education in Anaesthesia, Critical Care & Pain, vol. 9, No. 4, pp. 130-135, 2009.

Korkmaz et al., Pulsed radiofrequency versus conventional transcutaneous electrical nerve stimulation in painful shoulder: a prospective, randomized study, Clin Rehabil. Nov. 2010;24(11):1000-8, Aug. 4, 2010.

Lowry et al., Spinal Cord Stimulation for the Treatment of Chronic Knee Pain Following Total Knee Replacement, Pain Physician, 13:251-256, 2010.

(56) References Cited

OTHER PUBLICATIONS

Miller et al., Superimposed single impulse and pulse train electrical stimulation: A quantitative assessment during submaximal isometric knee extension in young, healthy men, Superimposed Electrical Stimulation Techniques, Muscle & Nerve, Aug. 1999, pp. 1038-1046.

Trends in the Health Wearable Technology, first available Oct. 26, 2021, mokosmart.com, [online], [site visited Mar. 7, 2025], Available from internet URL: https://www.mokosmart.com/health-wearable-technology-trends/ (Year: 2021).

* cited by examiner

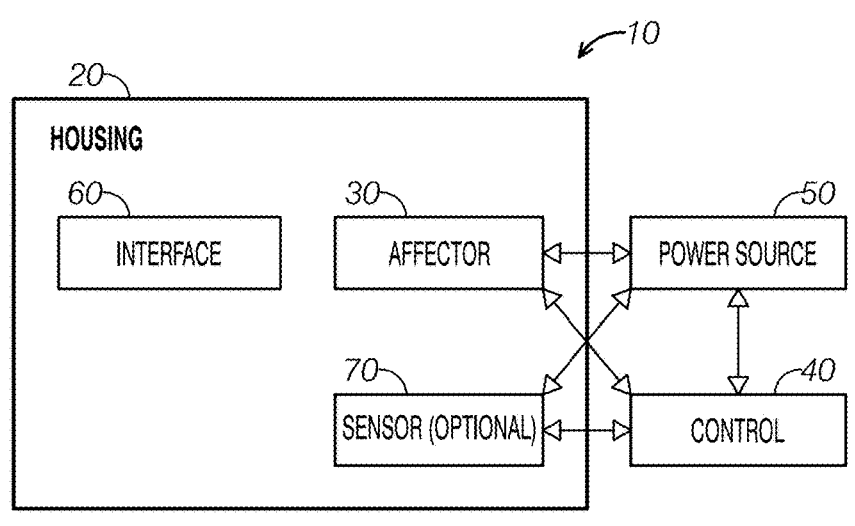
FIGURE 1
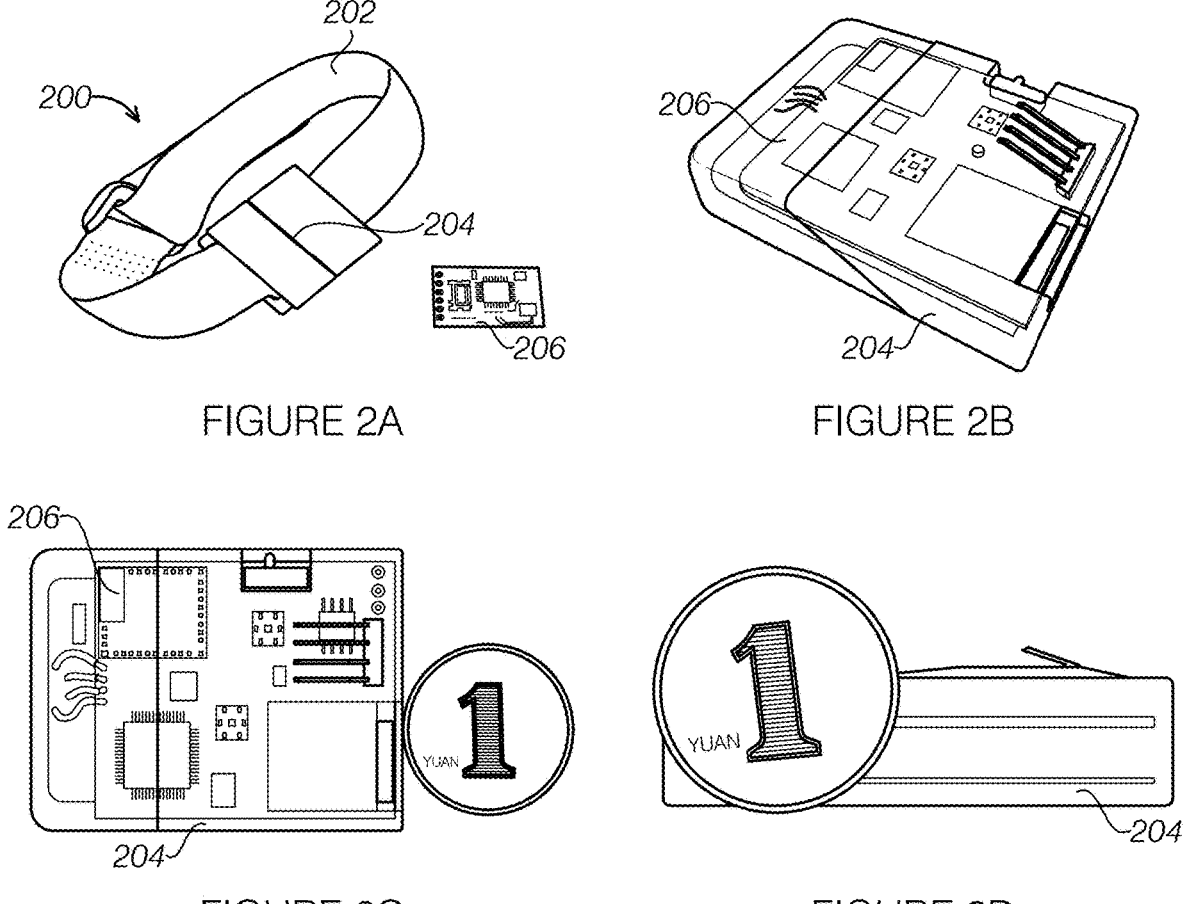
FIGURE 2A                                    FIGURE 2B
FIGURE 2C                                    FIGURE 2D

INDIVIDUALLY ADDRESSABLE ELEMENT (502)

500

600

UPPER (606)

COMPONENTS (602)

SOLE (604)

SCREW MECHANISM WITH PLUNGER(704)

HOUSING WITH GEL (706)

SKIN (702)

CONDUCTIVE GEL (700)

708

FRONT VIEW

METHOD - 1

METHOD - 2

JOG                                  JUMP

KNEE LOAD

TOTAL

DUE TO MUSCLES

STANCE PHASE

GASTROC
(2200)

2204

SOL (2202)

2204

CALF
MUSCLES

GASTROCNEMIUS
(2200)

SOLEUS
(2202)

ACHILLES TENDON

2204

A

KNEE LOAD

BEFORE

AFTER

STANCE PHASE

B

KNEE LOAD

BEFORE

AFTER

STANCE PHASE

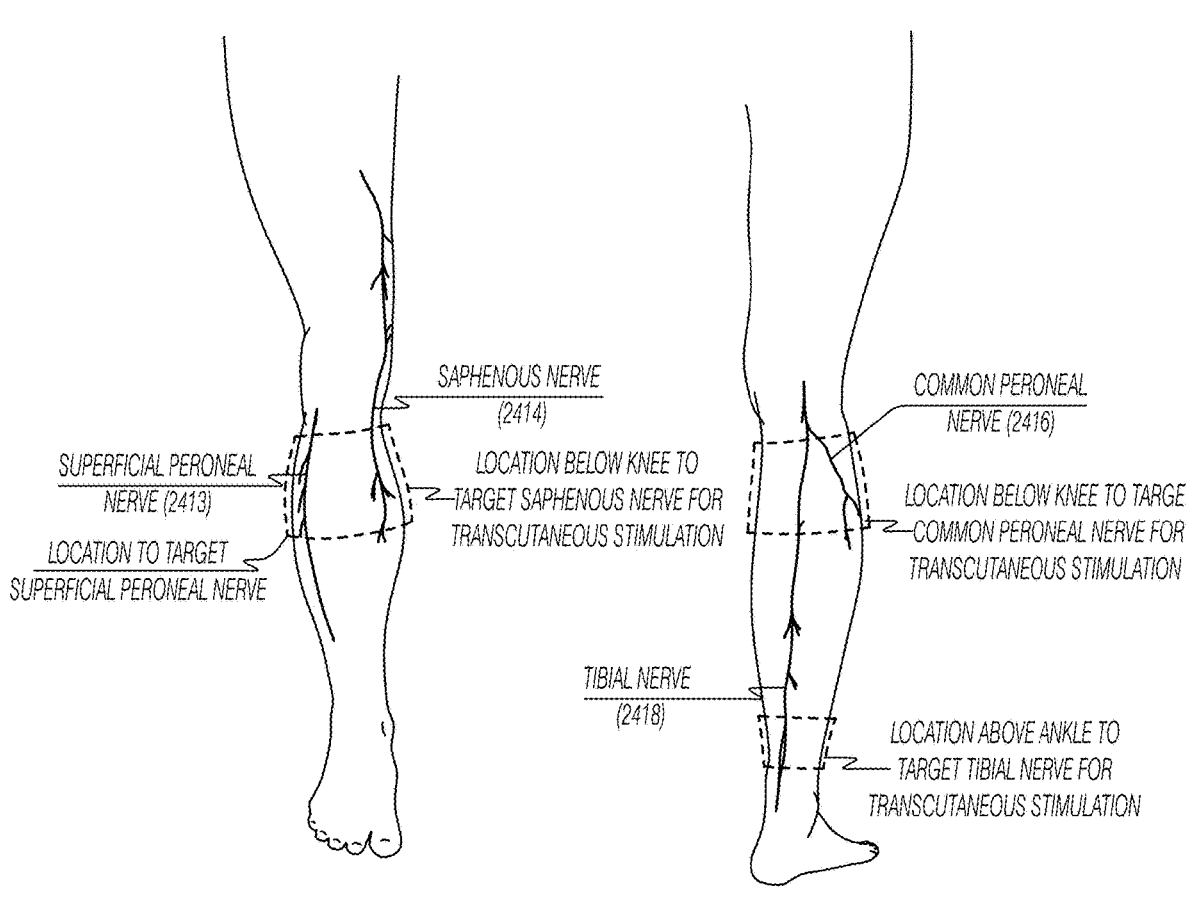
FIGURE 24G                    FIGURE 24H

SYSTEMS, DEVICES, AND METHOD FOR THE TREATMENT OF OSTEOARTHRITIS

CROSS REFERENCE TO RELATED APPLICATIONS

This application is a continuation of U.S. patent application Ser. No. 15/748,616, filed Jan. 29, 2018, which is the U.S. National Stage of PCT/US2016/045038, filed Aug. 1, 2016, which claims priority to U.S. Provisional Application No. 62/199,965, filed Jul. 31, 2015, and U.S. Provisional Application No. 62/276,797, filed Jan. 8, 2016, each of which is herein incorporated by reference in its entirety.

This application may be related to International Patent Application No. PCT/US2014/012388, filed Jan. 21, 2014, International Patent Application No. PCT/US2015/033809, filed Jun. 2, 2015, and PCT/US2016/037080, filed Jun. 10, 2016, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate to the treatment of osteoarthritis, and more particularly to gait retraining and/or modifying muscle activation patterns to treat knee pain associated with osteoarthritis.

BACKGROUND

Osteoarthritis (OA) is the most common form of arthritis, and both prevalence and incident rate increase with age. In the US, for adults over 30, symptomatic knee OA affects about 6% of the population. For ages 63-75, prevalence of knee OA increases to 11% of women and 7% of men. Pain in the knee due to a disease such as OA can have great functional impact and, especially among older adults, often reduces ability in activities of daily living (ADL) involving the legs, such as walking, transferring, and using the bathroom. OA causes more disability in walking and climbing stairs than any other disease and is the most common reason for total knee and hip replacement.

General knee pain has an even greater healthcare and societal impact. Two surveys assessing knee pain in older adults in the UK both estimated an annual prevalence of 25% for knee pain in older adults. In one of those studies, 15% of subjects in the general population aged over 55 have had restricted activity because of knee pain occurring on most days in one month during the past year.

In knee osteoarthritis, the medial compartment of the knee is affected ten times more often than the lateral compartment, which is likely due to greater medial compartment loading during gait to maintain knee joint stability. The first peak of the external knee adduction moment (KAM) is a surrogate measure of medial compartment loading, and has been correlated with pain and presence, severity, and progression of medial compartment knee osteoarthritis. Thus, treatments that reduce the KAM have the potential for reducing pain and slowing progression of osteoarthritis.

SUMMARY OF THE DISCLOSURE

The present invention relates to the treatment of knee pain associated with osteoarthritis, and more particularly to gait retraining and/or modifying muscle activation patterns to treat osteoarthritis.

The recent advances in the miniaturization of sensors, power sources, and stimulators, makes it possible to combine: (1) a feedback or cuing system to monitor an individual's gait kinematics and assist the individual in altering their gait by providing real-time feedback to the individual (e.g., visual, auditory, electrical, vibrational, etc.) without the need to visit a motion analysis laboratory, (2) an electrical nerve stimulation device that stimulates nerves around the knee from the skin surface to reduce the pain associated with OA, and/or (3) an electrical muscle stimulation device that alters muscle activation patterns based on measured EMG signals. There are four major challenges for providing effective feedback for gait modification; first, is to determine who may benefit from a gait change; second, determine the gait variable and target that will benefit an individual user; third, to accurately measure important gait variables and provide sensory feedback and/or stimulation to promote a more biomechanically effective walking pattern; and fourth, to effectively alter muscle activation patterns to reduce knee loads that have a chronic, long-term effect by initiating plastic adaptation of central neural circuits and/or reflex pathways associated with gait.

There are also two major challenges for surface stimulation; first, stimulating at the amplitudes required to effectively stimulate these deep nerves may cause pain or discomfort due to the stimulation of the cutaneous receptors; second, neuroanatomical variability between individuals make it difficult to appropriately position the stimulation electrodes from the surface. This system for reduction of knee pain can increase the exercise tolerance of an individual with knee OA, which could lead to increased knee strength, improved joint stability, and further reduction in knee pain.

In some embodiments, a system for reducing knee pain associated with osteoarthritis in an individual is provided. The system can include a wearable sensor for measuring a gait parameter, and a therapy device in communication with the wearable sensor. The therapy device can be configured to deliver a sensory stimulation based on the measured gait parameter that is configured to alter the individual's gait, where the sensory stimulation has a stimulation parameter that is proportional to a deviation of the measured gait parameter from a set range or value for the gait parameter.

In some embodiments, the sensory stimulation is electrical and is configured to not induce contraction of a muscle. In some embodiments, the electrical sensory stimulation is configured to enhance motor plasticity.

In some embodiments, the sensory stimulation is tactile or auditory.

In some embodiments, the sensory stimulation is configured to be provided in a fading feedback manner.

In some embodiments, the wearable sensor comprises an IMU or a force sensor.

In some embodiments, the gait parameter is foot progression angle, toe angle, ankle plantar flexion angle, step width, knee flexion angle, knee adduction angle, or knee adduction moment, knee flexion moment, or ankle plantar flexion moment, or any combination of these gait parameters.

In some embodiments, the wearable sensor and/or therapy device comprises a knee band, ankle band, leg band, sock, knee brace, knee wrap, foot wrap, ankle brace, knee brace, ankle wrap, shoe, shoe attachment, insole, compliant patch, pants, leg sleeve, knee sleeve, or ankle sleeve.

In some embodiments, a system for reducing knee pain associated with osteoarthritis in an individual is provided. The system can include a wearable EMG sensor for measuring an activation of a gastrocnemius muscle, and a therapy device in communication with the wearable EMG sensor. The therapy device can be configured to deliver a sensory stimulation based on the measured activation of the gastrocnemius muscle, where the sensory stimulation is configured to inform the individual of the activation of the gastrocnemius muscle.

In some embodiments, the system further includes a second EMG sensor for measuring an activation of a soleus muscle, where the wearable therapy device is configured to deliver a second sensory stimulation based on the measured activation of the soleus muscle, where the second sensory stimulation is configured to inform the individual of the activation of the soleus muscle.

In some embodiments, the system further includes a wearable sensor for measuring a key gait event.

In some embodiments, the gait event is selected from the group consisting of foot strike and toe off.

In some embodiments, the therapy device is configured to deliver a stimulation configured to reduce the activation of the gastrocnemius muscle.

In some embodiments, the therapy device is configured to deliver the stimulation based on the measured gait parameter.

In some embodiments, the therapy device is configured to deliver a stimulation configured to enhance the activation of a soleus muscle.

In some embodiments, the therapy device is configured to deliver the stimulation based on the measured gait parameter.

In some embodiments, a system for reducing knee pain associated with osteoarthritis in an individual is provided. The system can include a wearable sensor for measuring a gait parameter, a wearable EMG sensor for measuring an activation of a gastrocnemius muscle, and a therapy device in communication with the wearable sensor and the wearable EMG sensor. The therapy device can be configured to deliver a first sensory stimulation based on the measured gait parameter that is configured to alter the individual's gait and a second sensory stimulation based on the measured activation of the gastrocnemius muscle, where the first sensory stimulation has a stimulation parameter that is proportional to a deviation of the measured gait parameter from a set range or value for the gait parameter, and where the second sensory stimulation is configured to inform the individual of the activation of the gastrocnemius muscle.

In some embodiments, the therapy device is configured to deliver a third stimulation configured to reduce the activation of the gastrocnemius muscle.

In some embodiments, the therapy device is configured to deliver a fourth stimulation configured to enhance the activation of the soleus muscle.

In some embodiments, a system for reducing knee pain associated with osteoarthritis in an individual is provided. The system can include a wearable sensor for measuring a gait parameter, a wearable EMG sensor for measuring an activation of a soleus muscle, and a therapy device in communication with the wearable sensor and the wearable EMG sensor. The therapy device can be configured to deliver a first sensory stimulation based on the measured gait parameter that is configured to alter the individual's gait and a second sensory stimulation based on the measured activation of the soleus muscle, where the first sensory stimulation has a stimulation parameter that is proportional to a deviation of the measured gait parameter from a set range or value for the gait parameter, and where the second sensory stimulation is configured to inform the individual of the activation of the soleus muscle.

In some embodiments, the therapy device is configured to deliver a third stimulation configured to enhance the activation of the soleus muscle.

In some embodiments, the therapy device is configured to deliver a fourth stimulation configured to reduce the activation of the gastrocnemius muscle.

In some embodiments, the therapy device is wearable.

In some embodiments, the therapy device is a mobile phone or smart watch.

In some embodiments, a method for reducing knee pain associated with osteoarthritis in an individual is provided. The method can include measuring a gait parameter; determining a deviation of the measured gait parameter from a set range or value for the gait parameter; delivering a sensory stimulation to the individual based on the determined deviation of the measured gait parameter; and altering the individual's gait kinematics such that the deviation of the measured gait parameter is reduced in subsequent measurements of the gait parameter.

In some embodiments, the gait parameter can be foot angle, step width, knee angle, and knee adduction moment.

In some embodiments, the set range or value is predetermined.

In some embodiments, the sensory stimulation is delivered in a fading feedback manner.

In some embodiments, the sensory stimulation is electrical and is configured to not induce contraction of a muscle.

In some embodiments, the electrical sensory stimulation is configured to enhance motor plasticity.

In some embodiments, the method further includes measuring an activation of the gastrocnemius muscle; and delivering a second sensory stimulation based on the activation of the gastrocnemius muscle to inform the individual of the activation of the gastrocnemius muscle.

In some embodiments, the method further includes measuring an activation of a soleus muscle; and delivering a third sensory stimulation based on the activation of the soleus muscle to inform the individual of the activation of the soleus muscle.

In some embodiments, the method further includes delivering a stimulation configured to reduce an excitability of the gastrocnemius muscle.

In some embodiments, the method further includes delivering a stimulation configured to enhance an excitability or activate a soleus muscle.

In some embodiments, the method further includes measuring an activation of the gastrocnemius muscle; measuring an activation of a soleus muscle; delivering a second sensory stimulation based on the activation of the gastrocnemius muscle to inform the individual of the activation of the gastrocnemius muscle; delivering a third sensory stimulation based on the activation of the soleus muscle to inform the individual of the activation of the soleus muscle; delivering a stimulation configured to reduce an excitability of the gastrocnemius muscle; and delivering a stimulation configured to enhance an excitability or activate a soleus muscle.

In some embodiments, a method for reducing knee pain associated with osteoarthritis in an individual is provided. The method can include measuring a plurality of gait parameters;

determining a deviation of each of the measured gait parameters from a set range or value for each of the gait parameters; prioritizing the plurality of gait parameters based on the determined deviations; identifying a high priority gait parameter based on the step of prioritizing the plurality of gait parameters; delivering a sensory stimulation to the individual based on the high priority gait parameter; and altering the individual's gait kinematics.

In some embodiments, the sensory stimulation is delivered to a peripheral nerve in the leg.

In some embodiments, the sensory stimulation is delivered to a sensory nerve in the leg.

In some embodiments, a method for reducing knee pain associated with osteoarthritis in an individual is provided. The method can include measuring a plurality of gait parameters; measuring activation of the gastrocnemius muscle; determining a deviation of each of the measured gait parameters from a set range or value for each of the gait parameters; prioritizing the plurality of gait parameters based on the determined deviations; identifying a high priority gait parameter based on the step of prioritizing the plurality of gait parameters; comparing the identified high priority gait parameter with the measured activation of the gastrocnemius muscle; delivering a sensory stimulation to the individual based on the comparison of the high priority gait parameter with the measured activation of the gastrocnemius muscle; and altering the individual's gait kinematics or muscle pattern activation.

In some embodiments, the stimulation parameter is amplitude, frequency, pulse width, duration, or waveform shape.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a schematic diagram illustrating some embodiments of a system to modify human gait kinematics and/or modify muscle activation patterns.

FIGS. 2A-2F illustrates an embodiment of a wearable system and device.

6

Figure 13:
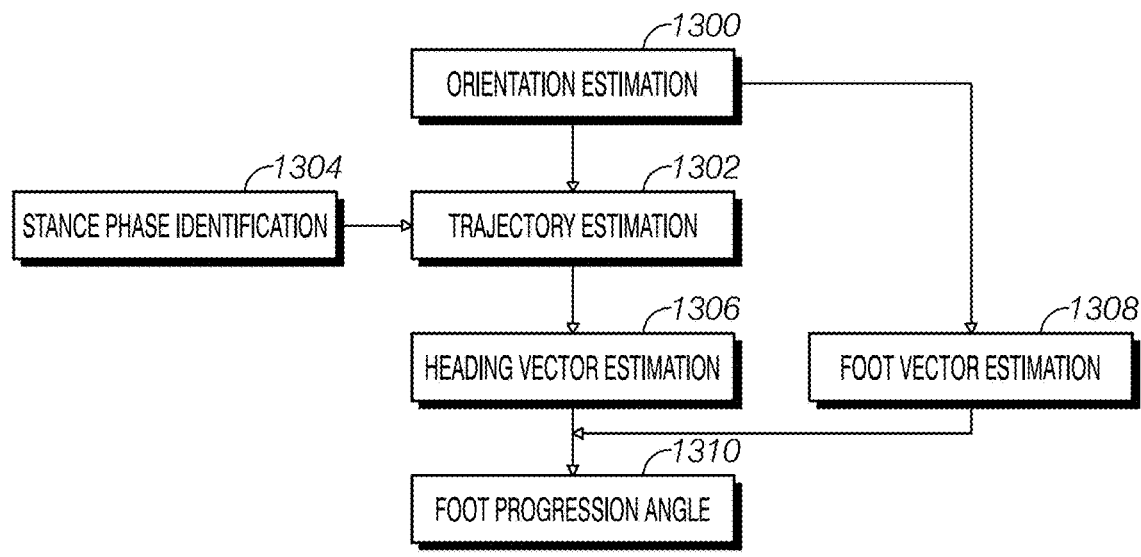

FIG. 13 illustrates a flowchart of an embodiment of a method to determine various gait parameters.

FIGS. 14A-14D illustrate various techniques for determining various gait parameters.

Figures 14A, 14B, 14C, 14D, 15:
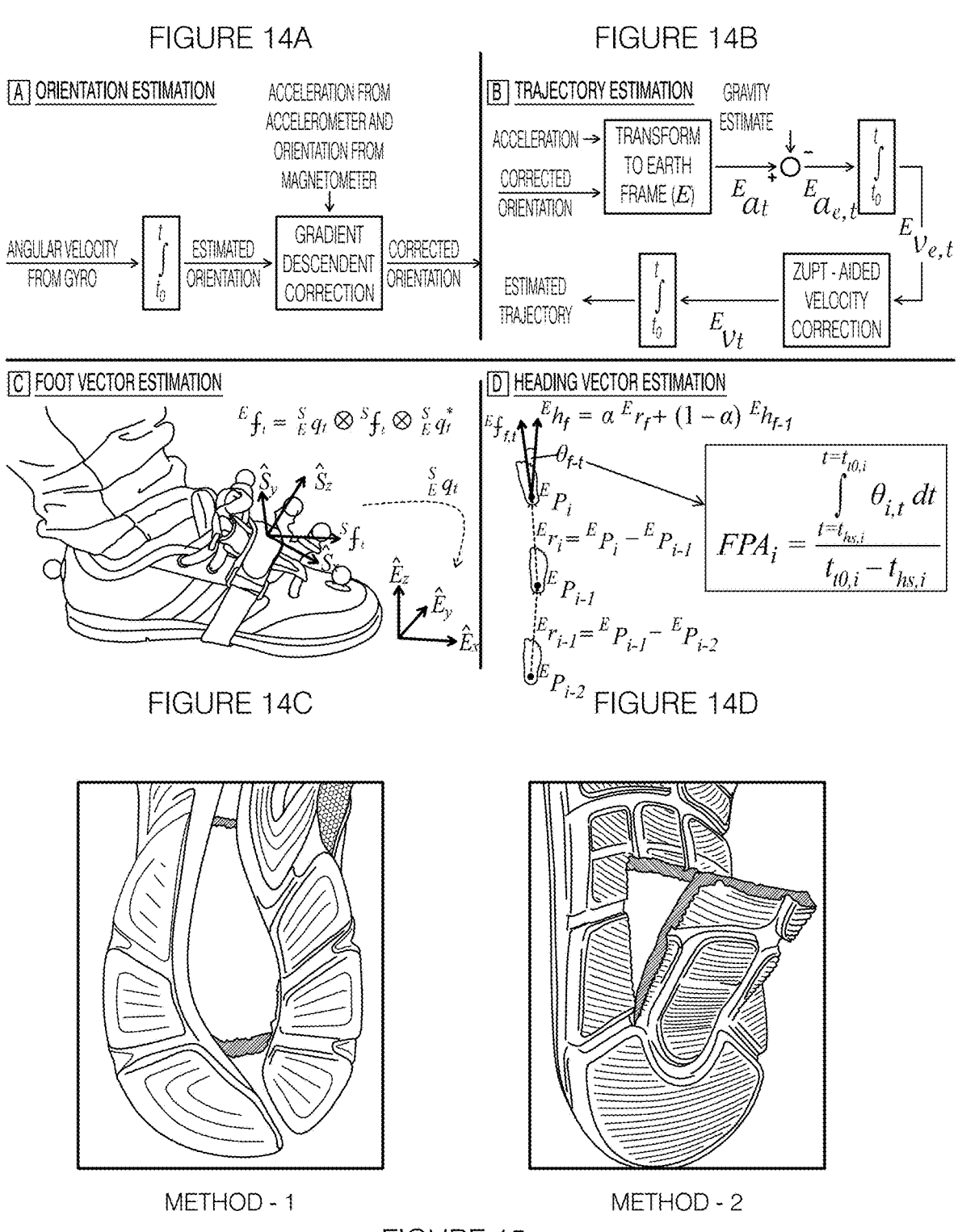

FIG. 15 illustrates various embodiments of a device inserted into the sole of a shoe.

Figure 16:
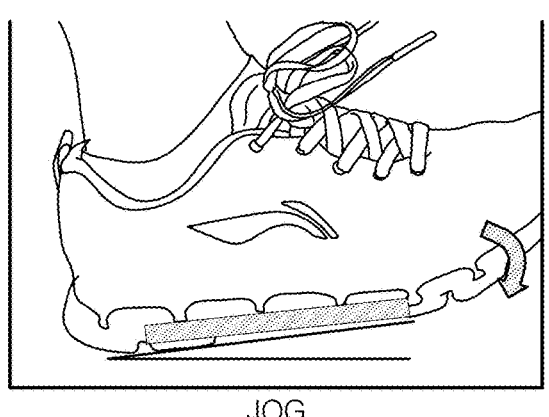
Figure 16:
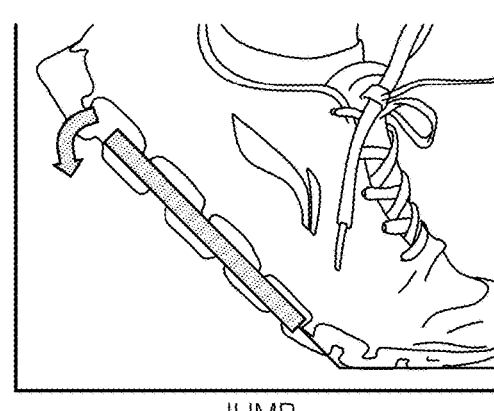

FIG. 16 illustrates the mechanics of the foot during gait.

Figure 17A:
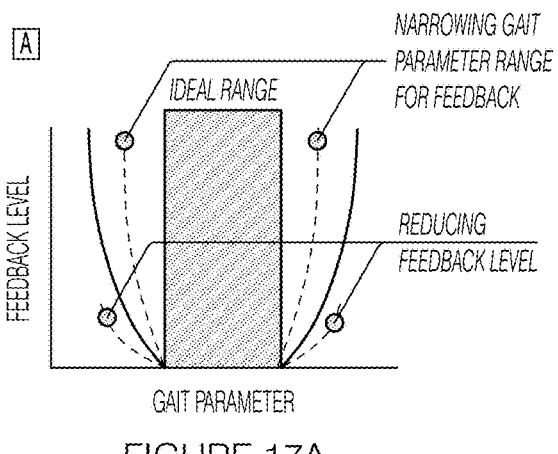
Figure 17B:
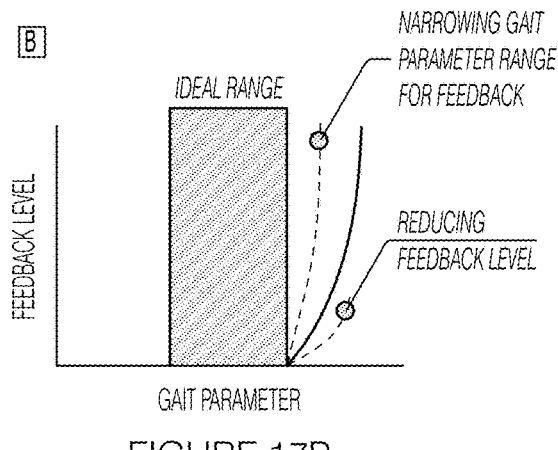

FIGS. 17A and 17B illustrate embodiments of responsive feedback and fading feedback.

Figure 18:
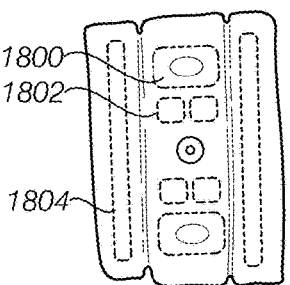

FIG. 18 illustrates an embodiment of the system and device where the therapy unit and sensor unit are incorporated into a single wearable device.

Figure 19:
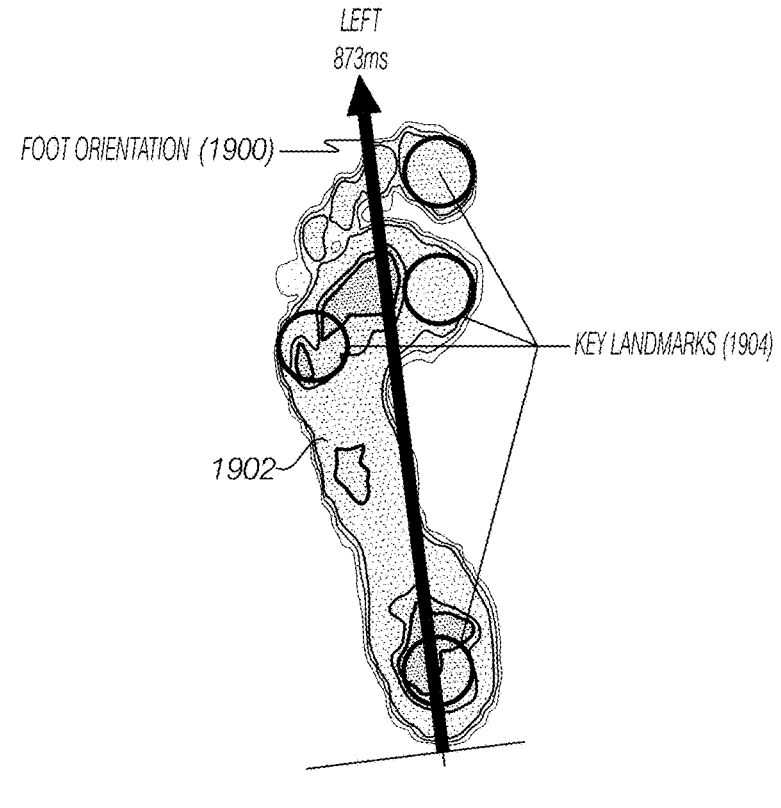

FIG. 19 illustrates a way to determine foot orientation from a foot pressure map.

Figure 20:
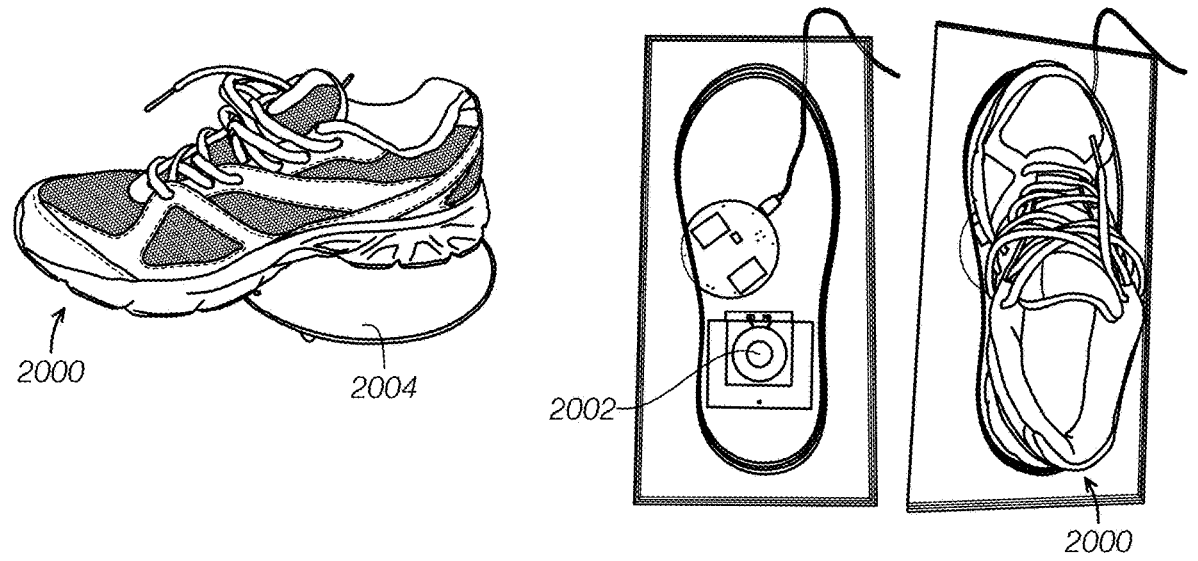

FIG. 20 illustrates another embodiment of a system and device that has been integrated into a shoe.

Figures 21, 22A, 22B, 22C, 23A, 23B:
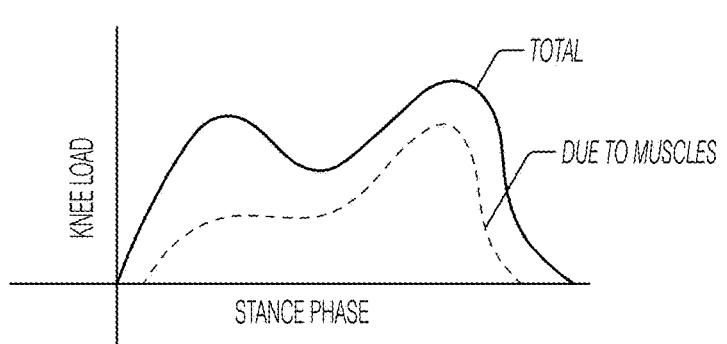

FIG. 21 illustrates knee load during walking.

FIGS. 22A-22C illustrates various muscles in the leg that are used during walking that can contribute to knee load.

FIGS. 23A and 23B illustrate the reduction in knee load from applying embodiments of the therapy described herein.

FIGS. 24A-24H illustrate various locations on the body that can be target by the systems and devices described herein.

DETAILED DESCRIPTION

"Electrical stimulation" refers to the application of electrical signals to the soft-tissue and nerves of the targeted area. Applying a "vibrotactile stimulation" refers to the application of a vibrational load to the soft-tissue and nerves and mechanoreceptors of the targeted area.

The systems, devices, and methods of this disclosure each have several innovative aspects, no single one of which is necessarily solely responsible for the desirable attributes disclosed herein. The present disclosure describes devices, methods and systems for (1) modifying or altering gait kinematics (or motion) via sensory augmentation and/or (2) modifying muscle activation patterns via augmented motor learning to slow the progression of and/or reduce the pain associated with knee OA, particularly during gait (e.g., walking, running, stair climbing, etc.). In some embodiments, peripheral nerve stimulation is used in conjunction with monitoring gait kinetics and kinematics and/or muscle activations, and providing real-time feedback to the individual. In some embodiments, a device is provided. Individuals with OA may have reduced proprioception and may therefore benefit from sensory augmentation therapies.

Additionally, repeated practice or exercise of a movement has been shown to elicit a plastic effect on in the brain, specifically in motor cortex. Repeated practice or exercise can be timed with electrical stimulation of specific nerves, muscles, reflex pathways, and/or motor cortex to enhance or accelerate the plastic effect. Thus, having an individual modify their gait kinematics in a specific, repeated practice can have lasting effect on gait patterns by retraining existing neural pathways in motor cortex or other parts of the central nervous system. To utilize this plastic change for the reduction of pain due to OA, a device will need to be sufficiently accurate and provide sensory feedback about specific gait variables to the individual at each step during the gait motion. This type of portable, wearable gait retraining system has not been possible in the past due to challenges in size, cost, and accuracy of sensors, especially portable, wireless sensors, power sources, and processors.

Stimulation applied to nerves and/or muscles can affect gait in multiple ways:

First, by direct muscle stimulation, when electrical stimulation is applied above muscle contraction thresholds and targets efferent nerves that innervate muscle or target muscle directly, this causes the muscle to contract and generate force to affect movement, similar to functional electrical stimulation (FES).

Second, by muscle re-patterning, stimulation is applied to afferent or sensory nerves that innervate muscle below muscle contraction threshold but above stimulation threshold of nerves; neuronal activity propagates to reflex circuits, like H-reflex, as well as back to the brain, especially motor cortex, and the central nervous system, causing plastic changes in the excitability of neural circuits and/or the muscles that drive regular gait patterns. Muscle re-patterning thus trains the wearer to transfer activation, and force, from one muscle (e.g., gastrocnemius) to another muscle (e.g., soleus) to unload the medial compartment during gait.

Third, by sensory augmentation, stimulation signals are applied to afferent or sensory nerves to lead a person to correct the motion causing pain. In OA, there is a delay between when a person performs the motions that overload the knee and experiences the resulting pain. Sensory augmentation uses sensory feedback to passively provide feedback to the central nervous system that causes someone to correct their motion. For example, in knee pain associated with OA, affectors may be positioned on the bottom or sides of the foot along the femoral and tibial distributions to provide sensory feedback to toe-in or toe-out. This may be less mentally taxing than cuing, and also more efficiently entrain sensory-motor circuits to produce motor plasticity in limb cortical areas. The electrical stimulation of the sensory nerves may also lead to stimulation of limb cortical areas of the brain that enhance motor plasticity and help an individual learn a new gait more quickly.

The device and system can use one or any combination of the above concepts to modify a person's gait to reduce pain and progression of OA.

Systems and Devices for Treating OA

FIG. 1 is a conceptual diagram illustrating some embodiments of a system 10 to modify human gait kinematics and/or modify muscle activation patterns. The System 10 includes a Housing 20, either flexible or rigid, one or more Affectors 30, one or more Controls 40 in electrical communication with the Affector 30, and one or more Power Sources 50. The Affector 30 can be, for example, an electrical nerve stimulator, vibrotactile stimulator, an implanted electrical nerve stimulator, and/or any device capable of delivering a nerve affecting signal. The Housing 20 can, in some embodiments, include an Interface 60. The Interface facilitates the coupling of the Affector to the subject. For example, the Interface can provide a physical, electrical, and/or chemical connection or point of contact to the subject. Further aspects and embodiments of the present invention are set forth herein. These and other aspects and embodiments of the invention are described in greater detail below, with reference to the drawing figures.

In some embodiments, the device is a wearable device with an electrically conductive skin interface that excites the underlying nerves from a transcutaneous surface stimulator. The device may be sized for a range of user sizes with stimulation electrodes positioned to target the appropriate nerves, as in the device described by International Patent Application No. PCT/US2014/012388, International Patent Application No. PCT/US2015/033809, and International Patent Application No. PCT/US2016/037080.

In another embodiment, the device and system is a wearable device with an electrically conductive skin interface that excites the underlying nerves from a transcutaneous surface stimulator and has embedded motion sensors (e.g., accelerometers, gyroscopes, magnetometer, bend sensors) and/or force sensors (e.g., strain sensors or pressure insoles) that measure the wearer's gait kinematics (e.g., toe-in angle) and/or kinetics (e.g., ground reaction force or knee joint loads) and store the data to a memory unit either on the device or in a separate unit that communicates via a wired or wireless connection.

In one embodiment as illustrated in FIGS. 2A-2E, the system and device is a wearable unit 200 that includes a wearable strap or band 202 and housing 204 for holding electronics 206. The electronics 206, shown in FIG. 2E can include one or more inertial measurement units (IMU) 208 (e.g., motion sensors such as accelerometers, gyroscopes, magnetometers, bend sensors), force sensors (e.g., strain sensors), muscle and/or nerve activity sensors (e.g., electrodes to measure EMG or microneurography) that communicate with a device control unit that processes measurement data to calculate one or more key gait parameters, such as gait kinematics (e.g., foot-progression angle, knee angle, step width etc.), kinetics (e.g., ground reaction force), muscle activation, or conduction of pain signals to the central nervous system. The electronics 206 can also include a processor 210 and memory 212 for storing instructions, that when executed by the processor, perform the algorithms, calculations, and steps described herein. The memory 212 can also store data gathered by the sensors and store information regarding the use of the device, including how and when the device delivered stimulations or cues to the individual, for example. The electronics 206 can also include a power supply 214 and power regulator 216 to power the various electronic components, and a communications module 218, which can be wireless, to communicate with other sensors, wearable devices, or computing devices such as mobile phones, tablets, or computers.

In another preferred embodiment, the device also houses one or more affectors to provide sensory feedback, which could be in the form of electrical stimulation through electrodes, vibration (e.g., vibration motor), auditory (e.g., speakers or headphones), tactile (e.g., skin stretch), or visual (e.g., LEDs on device, smartphone screen, or glasses).

Figure 2E:
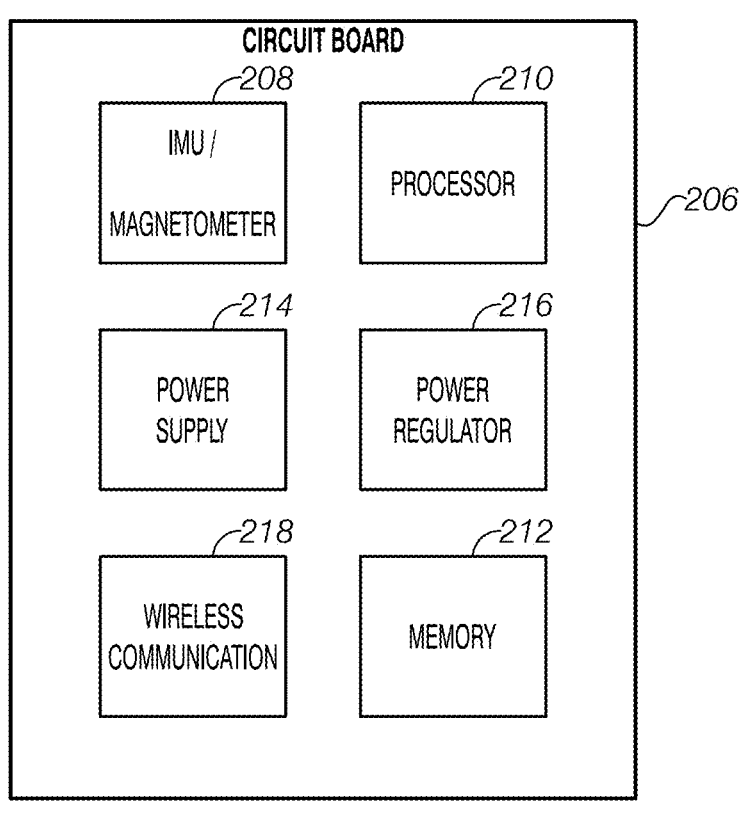
Figure 2F:
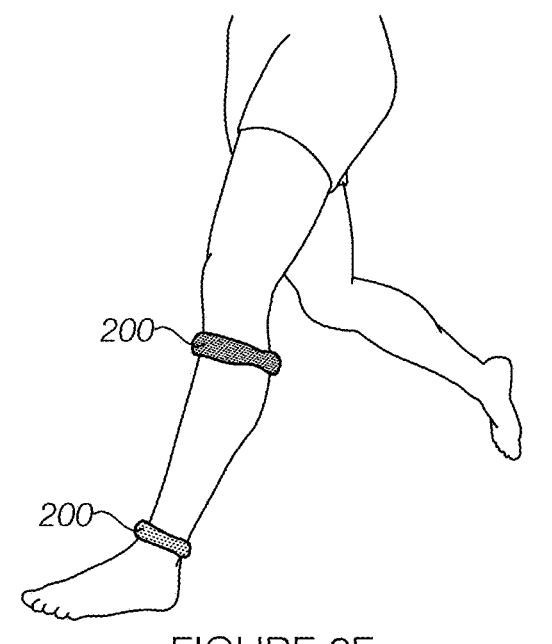

In some embodiments as shown in FIG. 2F, the device and system includes one or more wearable devices 200 with an electrically conductive skin interface for transcutaneous nerve stimulation, embedded measurement sensors, and sensory feedback units (i.e., cuing, muscle repatterning, and/or sensory augmentation) that notify the wearer of deviations in gait variables. In this embodiment, the device includes two separate units that communicate by wired connection or wireless communication (e.g., low-energy Bluetooth). Gait deviations can be calculated with data from embedded motion sensors and the device control unit. Sensory feedback to the wearer could be in the form of vibrotactile sensation (e.g., vibration motors), auditory sensation (e.g., speakers), tactile sensation (e.g., skin stretch or band tightening), electrical stimulation of peripheral nerves such as the tibial nerve or other sensory nerves, or other standard forms of haptic feedback. The feedback system could also notify the wearer of key events based on analysis of biological measures, including, but not limited to, prediction of pain level increase. The system, which may include cuing, could also notify the wearer of other predetermined events or reminders set by the wearer. An advantage of the system is that information can be communicated to the wearer real-time during activities, such as walking, running, or stair climbing. Instead of or in addition, the device can provide stimulation or modulate the stimulation to retrain gait such that the feedback is provided less frequently or at a decreased intensity level until it is no longer needed, referred to hereafter as fading feedback, as further described herein with respect to stimulation that promotes learning, for example.

In some embodiments, the sensor(s) and affector(s) may be combined into a single device, or they may be separate devices, wherein they are capable of rapid wireless or wired communication, as illustrated in FIG. 2F.

In some embodiments, the wearable unit houses an electrical stimulation unit that is connected to the wearer's skin through an electrically conductive skin interface to provide transcutaneous stimulation. In a further extension, the stimulation unit may have a logic controller that adjusts stimulation parameters (e.g., stimulation amplitude, frequency, waveform, etc.) based on sensor measures and/or calculated gait parameters.

Figure 3:
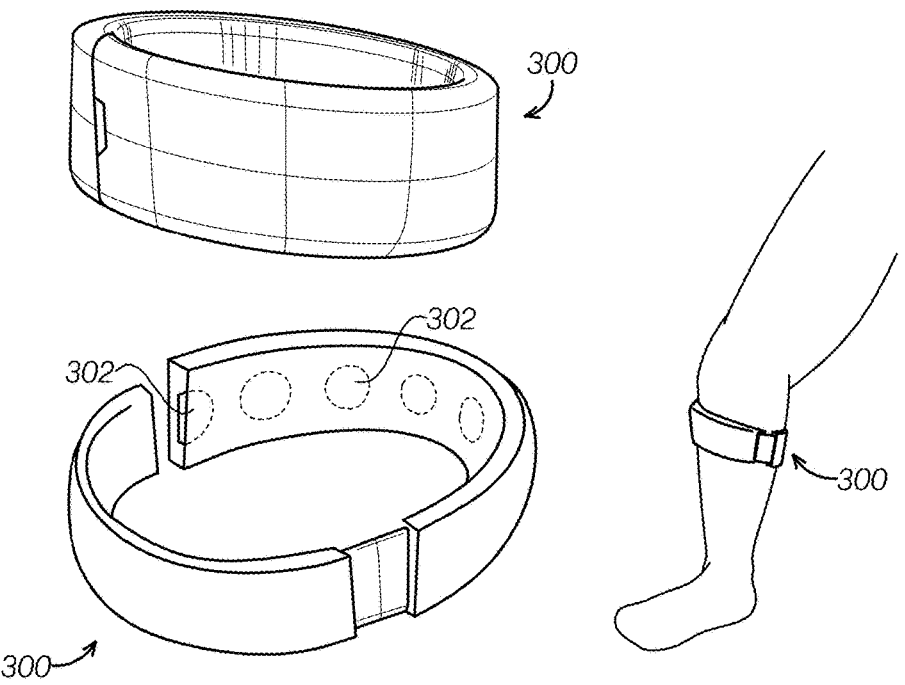
FIG. 3 illustrates another embodiment of a wearable system and device.

In some embodiments as shown in FIG. 3, the wearable device 300 includes a linear array of stimulation affectors (e.g., electrical or vibrotactile) 302 that are circumferentially distributed in a band that is intended to be worn around the leg, such as the calf, the knee, the ankle, or the thigh. The stimulation affectors are driven in a timed pattern to give the wearer a sense of direction to alter their gait. For example, the affectors could be driven in a clockwise pattern to inform the individual to toe-out while walking, and the motor could be driven in a counter-clockwise pattern to indicate toe-in gait.

Figure 4:
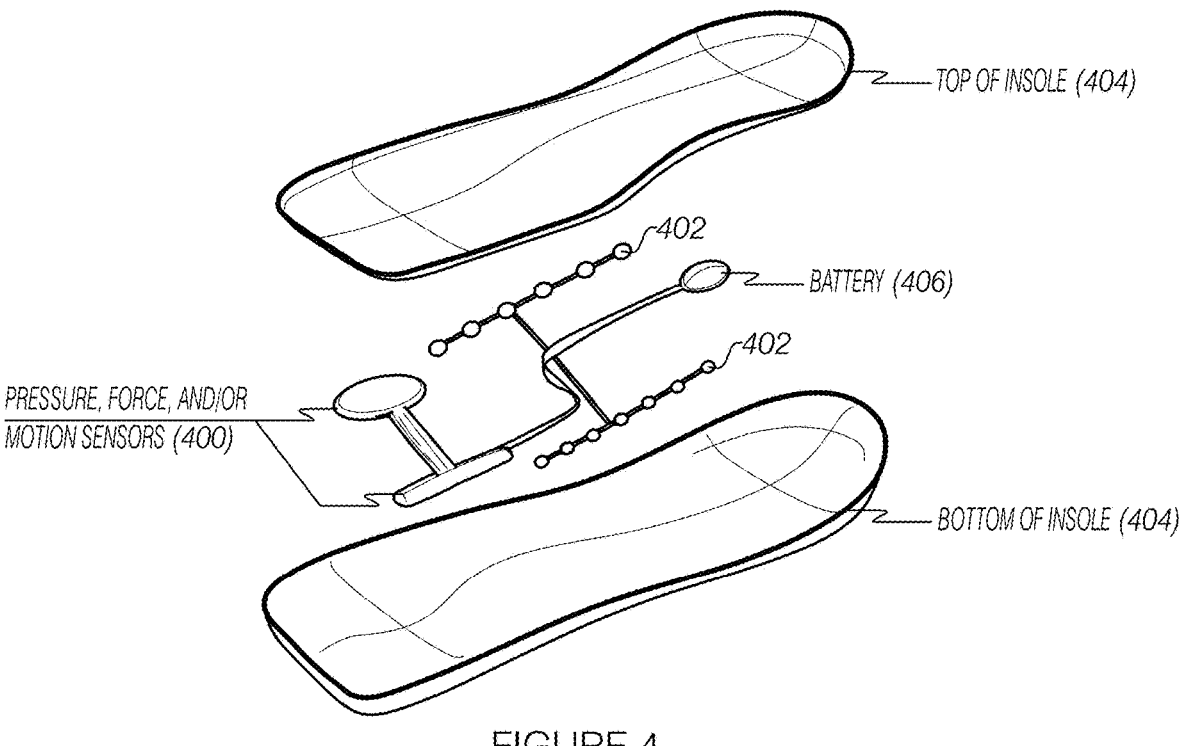
FIG. 4 illustrates an embodiment of a system and device that can be embedded or integrated into a shoe.

In some embodiments as shown in FIG. 4, the system can include a measurement unit 400 and a cuing unit or stimulation unit 402 that are embedded into an insole 404 that is inserted into the individual's shoe. The insole can have pressure sensors, such as strain or piezoelectric sensors, to measure ground reaction pressure or force of the individual, and could have accelerometers, gyroscopes, and magnetometers to measure the position and orientation of the individual's lower limb. The insole can also have an array of stimulation affectors to provide feedback, which may include cuing, to the individual. Affectors could be oriented in two arrays longitudinally on the medial and lateral side of the foot to indicate direction to the individual; or motors could be oriented transversely across the ball of the foot to indicate direction. In some embodiments, the system can have electrodes for providing electrical stimulation, vibration motors for vibrotactile stimulation, or speaker(s) for providing auditory stimulation. The system can also include a battery 406 and electronics as described herein.

In some embodiments, the wearable unit with measurement sensors (e.g. FIG. 2B-D) could be embedded into the sole of a shoe, as shown in FIG. 15. Ideally, measurement sensors that incorporate rigid components (e.g., circuit board or battery) are embedded under the heel, as this location undergoes less strain due to bending of the foot and shoe during gait, as illustrated in FIG. 16.

In some embodiments, the wearable device can use a plurality of sensors to collect, store, and analyze biological measures about the wearer including, but not limited to, motion (e.g., accelerometers, gyroscopes, magnetometer, bend sensors), ground reaction force or foot pressure (e.g., force sensors or pressure insoles), muscle activity (e.g., EMG), cardiovascular measures (e.g., heart rate, heart rate variability), skin conductance (e.g., skin conductance response, galvanic skin response), respiratory rate, skin temperature, and sleep state (e.g., awake, light sleep, deep sleep, REM). Using standard statistical analysis techniques, such as a logistical regression or Naïve Bayes classifier, these biological measures can be analyzed to assess a person's state, such as activity, such as sedentary versus active, and muscle usage, which in turn, can serve as a predictor for increases in pain levels.

In some embodiments, the measurement unit could employ accelerometers, gyroscopes, and/or a magnetometer attached to the individual's foot or ankle or shoe or sock to measure foot progression angle, which can be used to provide feedback to the individual about toe-in/toe-out of their gait. For example, measurement of progression angle can be calculated by taking the difference between foot orientation measured with gyroscopes and a heading direction determined from the magnetometer.

In some embodiments, the measurement unit could employ two sensors or two sets of sensors that measure step width (i.e., the lateral distance between steps) of the individual's gait. Step width could be measured by calculating position of each foot during a step from accelerometers, using a magnetometer to perform a dead reckoning correction of drift of the accelerometer. Step width could also be measured using a sonar or radar system where there is a unit attached to one foot sending and receiving a sonar signal and another unit attached to the opposite foot that reflects the signal; distance between the feet could be estimated as the feet pass by each other during the gait cycle.

In some embodiments, the wearable device can communicate with an external computer or device (e.g., tablet, smartphone, smartwatch, or custom base station) to transmit, store, and process data. Communication between the wearable device and external device can be a direct, physical connection, or with a wireless communication connection such as Bluetooth or GSM or cellular.

Figure 5:
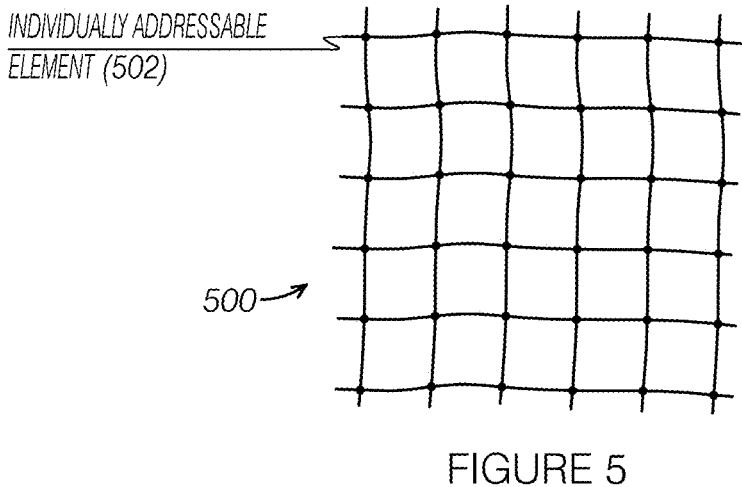
FIG. 5 illustrates an embodiment of an electrode array.

In some embodiments as shown in FIG. 5, the device contains a 2D or 3D array 500 of electrodes 502 such that the stimulation may be targeted. The elements of the array, the electrodes 502, may be individually addressable such that the location of stimulation can be adjusted on-the-fly or for each session, such as electronic referencing. Alternatively, the elements may be configured for an individual user, such as a mechanical configuration in which the electrode connections are cut or spliced to customize the device.

In some embodiments, the system communicates with an external, portable computational device, such as a smartphone via an app, or other mobile digital interaction. The device may be used to track information of relevant events either user entered or automatically captured from biological sensors, such as the time since the last knee pain, activity level, or joint load. In a further extension of this embodiment, this information may be used to close the loop to adjust stimulation parameters (waveforms, amplitude, on/off) or suggest user behaviors. In some embodiments, the system could centrally store biological measures from multiple wearers on a server system (e.g., the cloud), along with other relevant demographic data about each user, including age, weight, height, gender, ethnicity, etc. Data collected from multiple wearers is analyzed using standard statistical techniques, such as a logistic regression or Naive Bayes classifier (or other classifiers), to improve prediction of pain level increases by determining correlations between biological measures, activity level, and other recorded events. These correlations are used to set parameters of the stimulation waveform applied by the stimulation unit, determine best time to apply stimulation therapy, and/or adapt the stimulation waveform applied by the stimulation unit in real time. In addition, these correlations can be used to provide recommendations to the wearer about when to perform therapy or other techniques to reduce pain. In a further extension of this embodiment, the server system can also download and analyze information from the scientific literature to set parameters that adjust stimulation and/or recommendations to the wearer.

Figure 6:
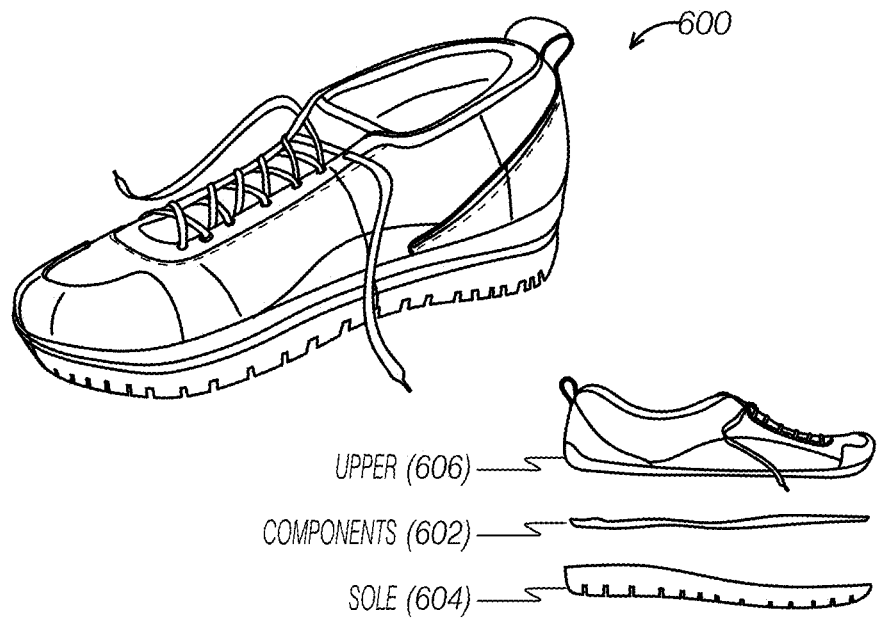
FIG. 6 illustrates another embodiment of a system and device that can be embedded or integrated into a shoe.

In some embodiments, the form of the device could be a knee band, ankle band, sock, knee brace, knee wrap, ankle brace, ankle wrap, shoe or shoe attachment, insole, compliant patch, pants, or a leg sleeve. For example, FIG. 6 shows an embodiment of the device which can include a stimulation and/or sensor unit that can be integrated and/or embedded into a shoe 600. For example, the electronic components 602 can be placed, for example, between the sole 604 and the upper portion 606 of the shoe. Other placement locations on the shoe include the heel or back portion of the shoe, the tongue of the shoe, or the upper portion of the shoe.

In some embodiments, the wearable device can have a processing unit that collects, stores, processes, and analyzes the biological measures, along with other data input by the wearer, such as logging activities or inputting body weight and other user characteristics.

In some embodiments, the wearable device can have a GPS or similar device to track the location and assess activity of the wearer. GPS measures can be combined with mapping or location systems to determine context of the wearer's activity (e.g., gym versus office) or determine changes in elevation during specific activities, such as running or stair climbing.

In some embodiments, the wearable device can track parameters about stimulation provided by the stimulation unit, including time of stimulation, duration of the stimulation session, and power used by the stimulation unit. This data can be stored on memory in the wearable device, processed by the wearable device, and/or transmitted to an external computing device.

In some embodiments, the stimulation unit can use switches or electrical sensor to detect connection of electrodes: to ensure proper and unique electrodes are being installed (i.e., not using a different or incorrect type of electrode) communicating a unique code, for example via RFID; to regulate the number of uses for each electrode to prevent over use; and to prevent the usage of the device without an electrode to prevent small shock.

In some embodiments, the system may include features to increase skin comfort. One solution is to use a high frequency carrier (kHz or greater) wave over the low frequency beats (10 to 200 Hz), or to position electrodes such that the interaction of two waveforms combines to produce a low frequency beat.

Figure 7:
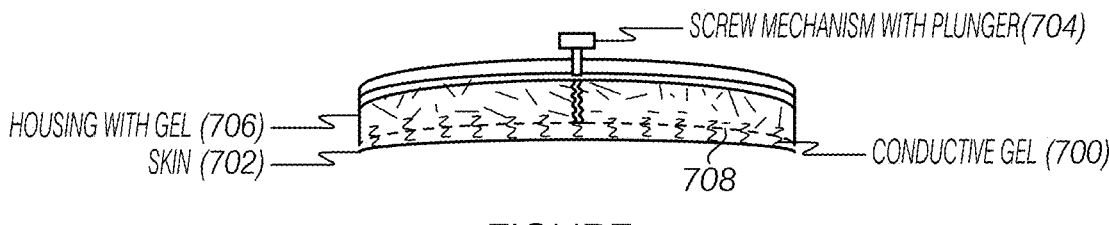
FIG. 7 illustrates an embodiment of the system and device with a dispensable conductive gel that can include a medication.

In some embodiments as shown in FIG. 7, lidocaine or a similar pain reducing compound (e.g., other analgesics or anesthetics) may be incorporated into an electrode hydrogel 700 to numb the skin surface 702 or desensitize the surface receptors to increase skin comfort. Alternatively, this chemical compound gel could be pushed out from the device similar to how deodorant is snap-clicked out from a deodorant stick, by using a screw mechanism with a plunger 704 that pushes the gel out of the housing 706 through channels 708 in the bottom of the housing that contacts the skin, for example. Another approach is to hypopolarize by initially hyperpolarizing using an excitatory agent like alpha hydroxyl sanshool.

In some embodiments, to improve skin comfort, the skin may be cooled by attaching an outer sleeve containing a cold material, such as a gel, or circulating a cold fluid in pipes housed in the sleeve.

In some embodiments, to improve skin comfort or improve perception of feedback, the wearable device could house a vibration motor to apply a vibrational stimulation simultaneously with electrical stimulation.

In some embodiments, the wearable device has the form of a sock, which is near-field powered by coupling between electronics and coils in the sole of a shoe and a coil in the sock.

Figure 8:
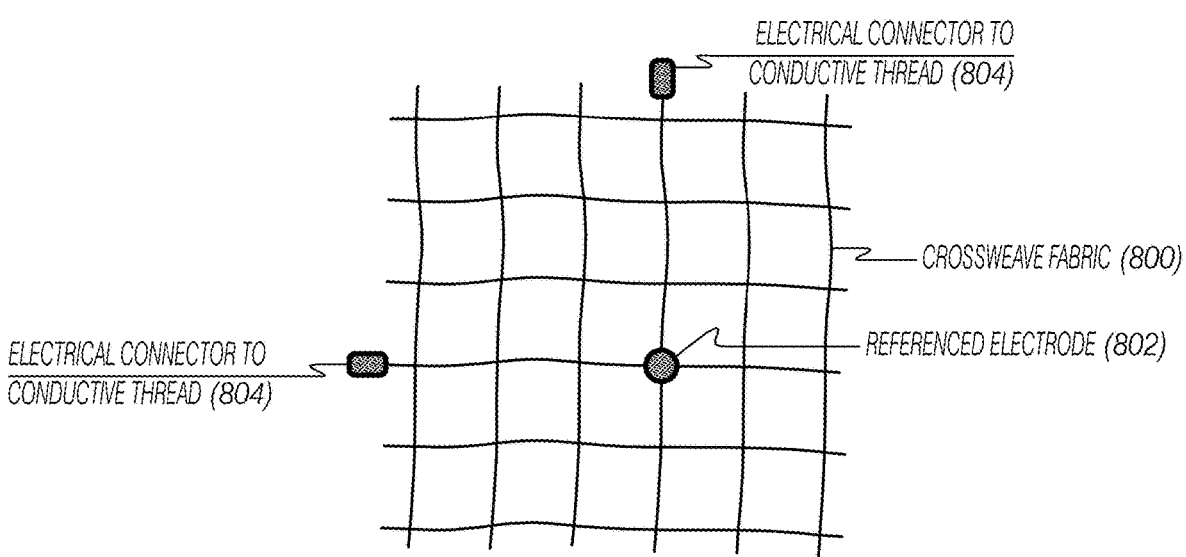
FIG. 8 illustrates another embodiment of an electrode array that can be made from a crossweave fabric.

In some embodiments as shown in FIG. 8, the wearable device is in the form of a sock, sleeve or other garment that contains an electrode array that can be formed from a crossweave fabric 800 in which a strip along the top or side of the fabric is referenced such that the electrode 802 is positioned at the intersection of the conductive threads, which can have electrical connectors 804 that can be put in electrical communication with a power source.

Figure 9:
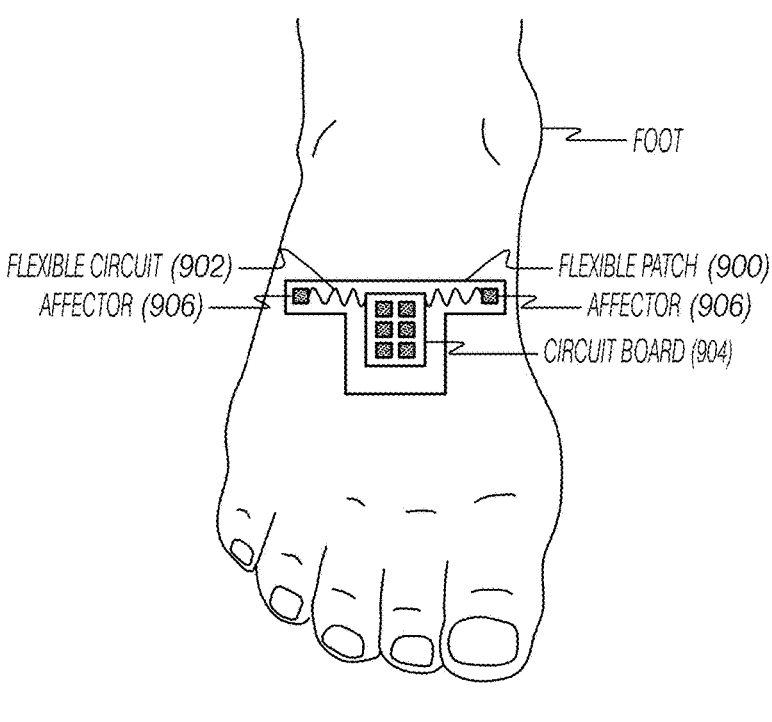
FIG. 9 illustrates an embodiment of a flexible device that can be affixed to a body part.

In some embodiments as shown in FIG. 9, the device is a flexible housing or patch 900 with an adhesive that adheres directly to the wearer's skin. This embodiment has a device with flexible circuitry 902, and a slim, light-weight design to not be cumbersome when worn on the body. Possible locations for the sticky patch could include the foot (either dorsal or plantar side) or on the shank/tibia close to nerves associated with reduction of knee pain, such as the saphenous nerve or tibial nerve. The flexible housing or patch 900 encloses or has a circuit board 904, such as the circuit board described in FIG. 2E and elsewhere, and one or more affectors 906. The affectors are in electrical communication with the circuit board via flexible circuits. The shape of the housing can improve repeatability of positioning the device, for example the widest portion of the housing can be aligned with the long axis of the foot. Additionally the t-shape illustrated allows the affectors to conform around the foot shape and provide physical separation of the affectors to allow distinct perception by the wearer.

In some embodiments, the housing could have a specific shape, for example a t-shape as illustrated in FIG. 9, to allow for easier alignment of the device on the foot, which improves estimation of foot orientation.

In some embodiments, the affectors are disposed in the flexible housing and attached to an electronics board with a flexible circuits FIG. 9, to allow for a flexible housing that conforms to the shape of the body part.

Figure 10:
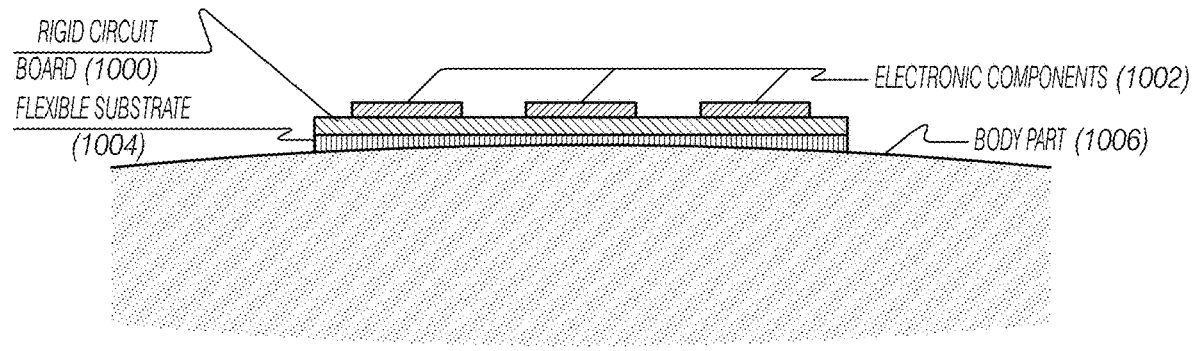
FIG. 10 illustrates another embodiment of a flexible device that has a flexible substrate that conforms to the body.

In some embodiments as shown in FIG. 10, the electronics board 1000 with various electronic components 1002 may be rigid and mount to a more flexible or elastic substrate material 1002, such as silicone or rubber, to allow the device to be worn on the body 1006 and conform to different body part shapes.

Figures 11A, 11B, 11C:
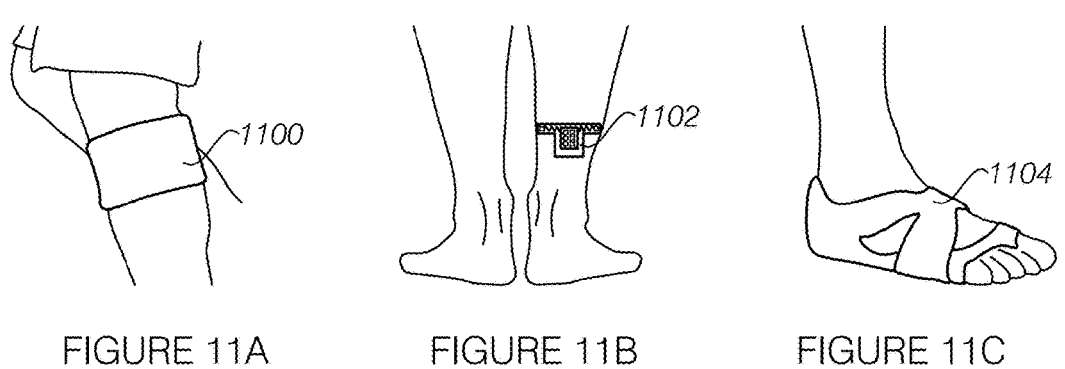
FIGS. 11A-11C illustrate various embodiments of the system device being worn on various body parts.
Figure 11D:
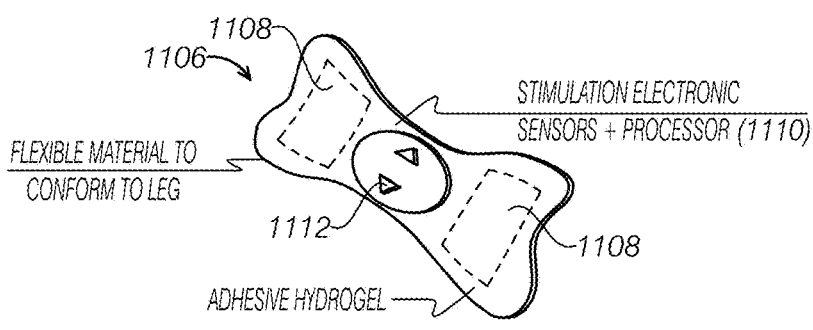
FIG. 11D illustrates an embodiment of a patch device.
Figure 12:
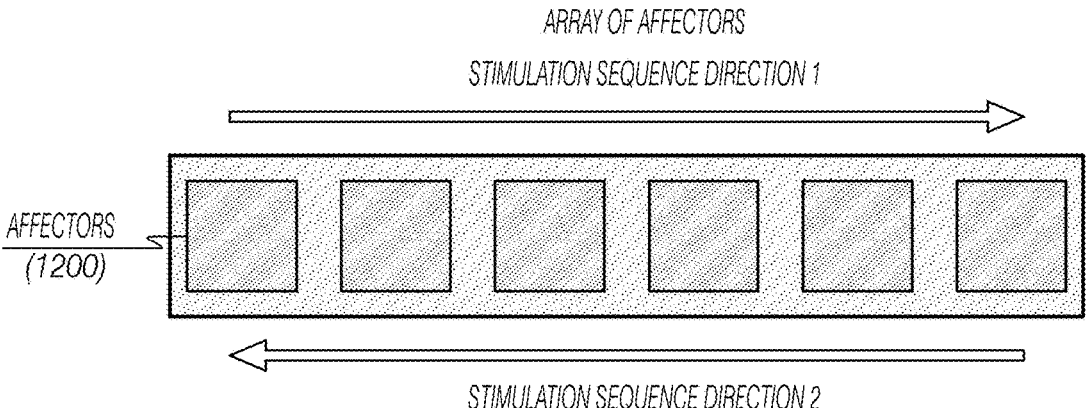
FIG. 12 illustrates an embodiment of a system and device with an array of effectors.

In other embodiments as shown in FIGS. 11A-11D, the device or system can have many form factors and can include any combination of the form factors described herein. For example, the device could be a fabric garment woven with conductive fabric. Fabric garments can contain electronic fabric with stretch-sensitive fibers for measuring limb position and displacement, and foot pressure, in addition to conductive pathways for electrical stimulation and embedded accelerometers. For example, as shown in FIG. 11A, the device can include a sleeve 1100 wrapped around an extremity, such as a sleeve wrapped around the leg just below the knee. The sleeve can slide on over the leg, or wrap and fasten around the leg with Velcro, snaps, or other common fasteners. FIG. 11B illustrates a flexible device that adheres to the skin like a patch 1102 or bandage, similar to FIGS. 9 and 10, where the device is adhered to the posterior side of the ankle, just above the Achilles' tendon. FIG. 11C illustrates a sock-like fabric garment 1104 worn on the foot. FIG. 11D illustrates a flexible patch 1106 with two electrodes 1108 to target a single nerve. The flexible patch can be coated with a conductive and adhesive hydrogel. The patch can be made of a flexible material, like silicone, to conform to body (e.g., behind knee). The center housing 1110 contains stimulation electronics, sensors, processor, and power source, for example. The housing 1110 may also include a basic user interface 1112 (i.e., one or more buttons) to control stimulation level and/or display information to user. The patch may or may not communicate wirelessly with an external device In some embodiments the device houses a single affector or a plurality of affectors. Specifically, a single affector would provide feedback to the wearer about a single task or direction (e.g., turn left), while two affectors could provide feedback about two tasks or directions (e.g., turn left or turn right). With two affectors, the affectors need to have enough physical separation to have distinct perception by the wearer. The specific minimum separation distance depends on the specific part of the body where the affectors are applied, the density of sensory receptors, and the type of stimulation. For vibration, a minimum distance can be as low as 15 mm, but preferably between 35-50 mm. Affectors 1200 can also be ordered in an array, for example linear or circular, and activated in specific sequences to convey directionality, as illustrated in FIG. 12.

In some embodiments, the affectors can be stimulated using different specific waveforms to convey a plurality of tasks or actions to the wearer. Waveform parameters that can be varied include amplitude, frequency, pulse width, and duration. Patterns of stimulation bursts can also be used as unique signals. Changes in waveforms need to be varied enough for the wearer to perceive unique sensory feedback signals.

In some embodiments, the device could contain an insole or woven fabric under the foot that can measure force or pressure between the foot and the ground. As shown in FIG. 19, a method to calibrate the orientation 1900 of the foot relative to the wearer's body can include calculating a foot pressure map 1902 from the sensor data after the wearer is instructed to stand in a predefined pose. Key landmarks 1904 from the pressure map 1902 are then identified to estimate the orientation of the foot.

In some embodiments, the wearable unit is in communication, either wired or wirelessly, with a separate stimulation unit that provides transcutaneous stimulation to a location different from that of the wearable unit.

In some embodiments as shown in FIG. 20, the wearable device 2000 has a portable, rechargeable power source, which is near-field powered by coupling between electronics and coils 2002 in the device (i.e., wireless charging) with a wireless charger 2004.

In some embodiments, the wearable unit stores data to a memory unit either on the device or in a separate unit (e.g., tablet, smartphone, smartwatch, or custom base station) that communicates through a wired connection or wirelessly (e.g., low energy Bluetooth or GSM).

In some embodiments, the wearable device can have a processing unit that collects, stores, processes, and analyzes the biological measures, along with other data input by the wearer. In some embodiments, some of the processing of the data can be performed on an external computing device or on the cloud.

In some embodiments, the electrodes for transcutaneous electrical stimulation are dry electrodes made from a conductive materials, such as metallic fabrics or conductive silicone. The systems, devices, and methods described herein allow the detection or determination of gait variables that are difficult for an individual to detect or sense, such as the adduction moment of the knee, and then provide the individual with sensory stimulation as a proxy for that gait variable, allowing the individual to modify aspects of their motion that are difficult to sense.

Although feedback stimulation can be provided on the leg, ankle, knee, and foot, location of the stimulation can also be positioned on different locations of the body, for example, audio or vibratory stimulation from an individual's smartphone or a smartwatch worn on the wrist.

Figures 24A, 24B, 24C, 24D, 24E, 24F:
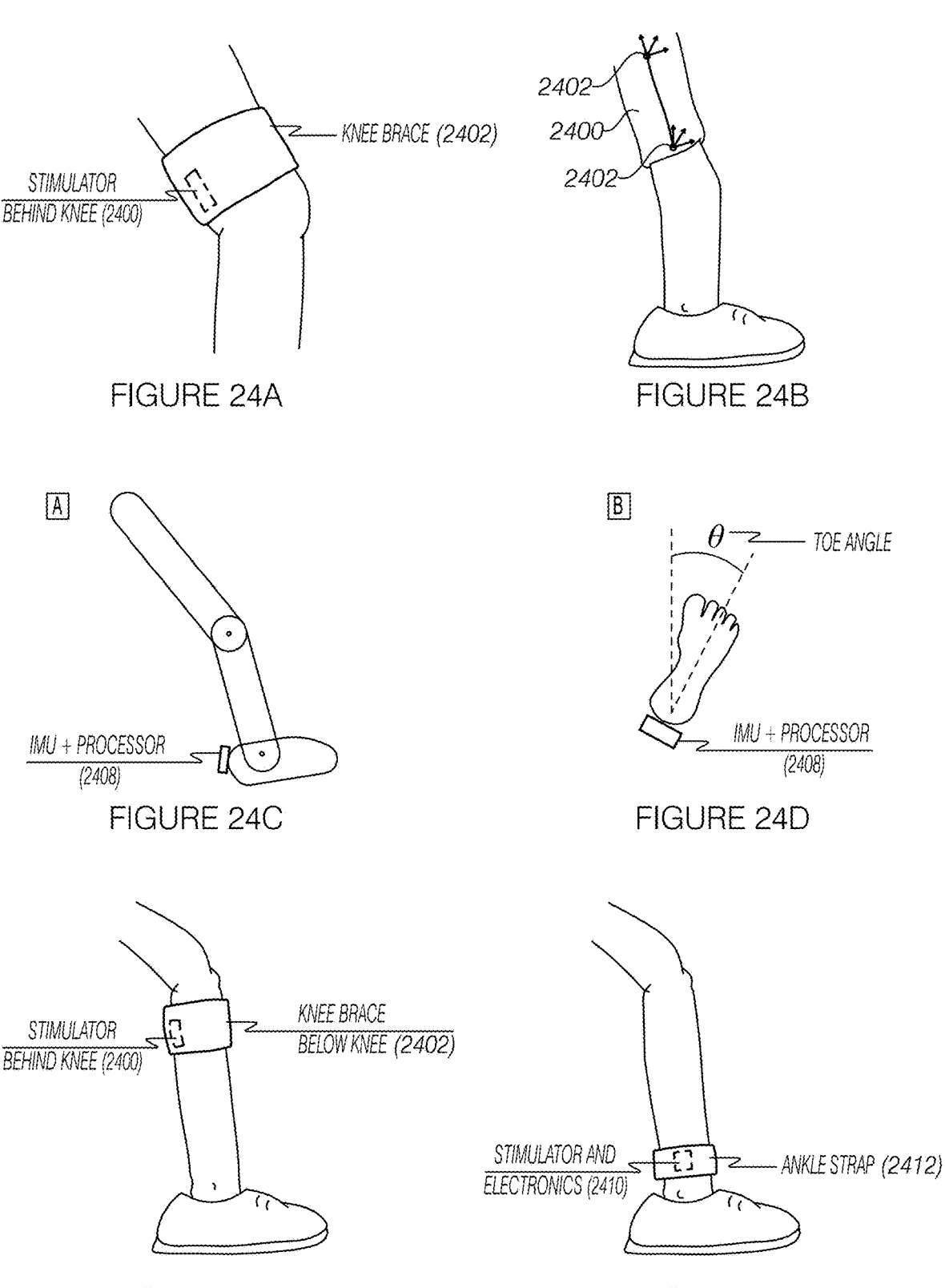

In addition to the locations of sensors and affectors described elsewhere in this application, FIGS. 24A-24H illustrate other locations where sensors and/or affectors can be positioned. For example, FIG. 24A illustrates positioning a stimulator 2400 on the upper leg and behind the knee using a knee brace 2402 or band or sleeve. FIG. 24B illustrates shorts 2404 with fiber optic sensors 2406. The fiber optic sensor extends from the persons trunk to the knee or joint of interest. The fiber uses three components of strain and twist in order to calculate the relative orientation of the joint of interest based on the detected orientation of the fiber. FIGS. 24C and 24D illustrate placing a sensor 2408 such as an IMU at the back of the heel or on the ankle to determine foot angle. The back of the foot or ankle is more stable than the top or toe portion of the foot. FIG. 24E illustrates placing a stimulator 2400 on the lower leg and behind the knee using a knee brace 2402 or band or sleeve. FIG. 24F illustrates placing a stimulator 2410 on the ankle using an ankle strap 2412. FIG. 24G illustrates the locations to stimulate the superficial peroneal nerve 2413 and the saphenous nerve 2414 on the leg. FIG. 24H illustrates the locations to stimulate the common peroneal nerve 2416 and the tibial nerve 2418 on the leg.

Method of Altering Gait Kinematics via Sensory Augmentation Therapy

For knee OA, the first peak of the external knee adduction moment (KAM) is often used as a surrogate measure of medial compartment loading and has been correlated with pain and the presence, severity, and progression of medial compartment knee OA. Multiple studies have also shown that individuals with OA can alter their gait kinematics to reduce the first peak of the KAM and reduce knee pain. For example, studies have shown that teaching individuals to walk with a toe-out gait or with a greater step width can reduce the peak of the KAM and/or reduce knee loads. However, these studies were performed in a controlled motion analysis laboratory with expensive motion tracking equipment that requires individuals with OA to return to the lab for training to learn the gait modifications that reduced their KAM. Therefore, in some embodiments, the key gait parameter(s) may be foot progression angle, step width, knee angle or a measure of KAM itself, for example. The systems and devices described herein can be used to determine the key gait parameters.

In some embodiments, the key gait parameter may be foot progression angle, which is defined as the angle between the foot vector and the heading vector (line of walking progression). The foot progression angle is determined in six steps as shown in FIG. 13. Orientation 1300 is estimated via the gradient descent algorithm, trajectory 1302 is estimated via strapdown integration, and stance phase identification 1304 is used with zero-velocity detection to correct velocity estimation drifts. The heading vector 1306 and foot vector 1308 are computed based on results of trajectory and orientation estimation, respectively, and the foot progression angle 1310 is the difference between these vectors in the horizontal plane.

As shown in FIG. 14A, sensor orientation is estimated with respect to the earth frame by integrating angular velocity, from a gyroscope for example, and then applying gradient descent correction with accelerometer and magnetometer data to get drift-reduced orientation estimation.

As shown in FIG. 14B, the foot trajectory is computed through double integration of the acceleration in the earth frame and is corrected via the zero-velocity assumption during stance. Zero-velocity estimation based on acceleration and gyroscope information to help estimate the stance period and implement a state-machine based approach for improved identification accuracy. In addition, heel strike events are detected from the accelerometer and gyroscope and the stance phase duration is approximated as 60% of the stride time.

As shown in FIG. 14C, the foot vector is estimated as the common vector fixed in an IMU-sensor frame. In other words, the foot vector is fixed with respect to the sensor frame S, then is transformed into the earth frame using the corrected orientation estimated from the previous step. Each subject performs dorsiflexion and plantarflexion motion of the ankle to calibrate the device.

As shown in FIG. 14D, the heading vector estimates the direction of forward movement by calculating a foot trajectory at each heel strike by subtracting the current foot trajectory from the foot trajectory at the previous heel strike. To improve heading vector estimation, a complementary filter parameter can also be applied to the foot trajectory at each stride. Finally, the foot progression angle (FPA) is computed as the difference between the heading vector and foot vector integrated over the stance phase of each step. In other words, the foot progression angle is computed as the average angle between the foot vector and heading vector during stance. The foot vector is computed at each time step, while the heading vector is estimated at each stride after heel strike. At each time step, an angle is defined between the foot vector and the heading vector projected onto horizontal plane parallel with the ground, and the foot progression angle for each step is the average of this angle during stance.

The above method was implemented with a wearable sensor and compared to measurements from an optical motion capture system on 13 subjects. The device and method exhibited accuracy similar with the motion capture system.

Step width can also be determined using the procedure described above, using a subset of the parameters and calculations described above.

KAM can be measured by measuring the ground reaction force and determining the position of the parts of leg. For example, the ground reaction force can be estimated or determined based on the body mass of the individual or by direct measurement using sensors in the shoe or bottom of the foot. The position of parts of the leg can be determined by placing and IMU or accelerometer on the upper leg and the lower leg and performing a double integration on the acceleration data to determine position.

In some embodiments as shown in FIG. 17A, the device provides feedback to the wearer when the calculated gait parameter deviates outside of a specified ideal range from step-to-step during gait in two different directions. Providing feedback in this manner can be accomplished with either two affectors or two distinct waveform patterns delivered by a single affector such that the wearer can discern between two different stimulations or cues. As shown, the magnitude of the feedback provided to the individual is related to or proportional to the magnitude of the deviation of the gait parameter from the ideal range.

In an extension of the previous embodiment as shown in FIG. 17B, the device provides feedback to the wearer when the calculated parameter deviates outside of the ideal range in one specific direction. This method for feedback could be useful when changes in gait parameter in only a single direction (e.g., toe-in versus toe-out) affect knee pain, and only requires a single affector delivering a single waveform pattern.

In some embodiments, the feedback can be stimulation to sensory nerves during gait to enhance sensory feedback of knee pain, or of a key variable associated with knee pain, such as foot angle, step width, knee angle, KAM, etc. In some embodiments, the sensory nerves are peripheral nerves located on the leg. In some embodiments, the stimulation may be subsensory, or may be a combination of sensory and subsensory stimulation, such as providing subthreshold electrical stimulation along with an audible or vibratory stimulation. In other embodiments, all the stimulation are above sensory threshold.

In another embodiment, the device is in communication with the affector(s) to apply stimulation to a predetermined or predetermined set or subset of nerves that provide sensory feedback to the central nervous system about pain and a sensor that measures activity of sensory nerves that cause pain (e.g., microneurography) and/or to block or modulate pain signals being sent to the brain. The affector(s) would apply stimulation that is above a threshold to activate sensory nerves, but below a threshold to contract muscle. Activating more sensory nerves associated with knee pain would provide augmented feedback to the central nervous system, which would elicit plastic changes. The affector(s) may be positioned on the femoral nerve to provide both sensory feedback and modulate pain signals, as the femoral nerve is a common site used for post-surgical nerve block. The affector(s) may also be positioned on the saphenous nerve, which is the distal branch of femoral nerve. The saphenous nerve is advantageous for sensory augmentation, as it is a sensory-only (non-motor) nerve. The affector(s) may also be positioned around the ankle to target the two major branches of the tibial nerve that reach the medial and lateral underside of the foot for sensory feedback.

In some embodiments, the device has user input that allows the wearer to input pain levels that is stored on a memory unit. In a further extension of this embodiment, the device adjusts stimulation parameters and/or provides feedback to the wearer based on history of pain levels. This is applicable to modifying muscle activation patterns described below.

In some embodiments, the feedback can be fading feedback such that at the beginning of treatment an enhanced or higher level or magnitude of stimulation is provided to the wearer, but as the treatment progresses, the level or magnitude of the stimulation is reduced as the wearer's gait improves. This promotes quicker learning of the desired gait kinematics that reduce KAM and/or knee pain. For example, FIGS. 17A and 17B illustrate various ways of providing fading feedback as treatment progresses. The dashed lines illustrate fading feedback, while the solid line represents the initial treatment feedback. For example, the feedback level for a given deviation of the gait parameter from the ideal range can be reduced, which is shown in the lower dashed lines. Alternatively, feedback may only be provided to smaller deviations of the gait parameters as treatment progresses, while either keeping the feedback level the same for a given deviation, or increasing the feedback level for a given deviation, or decreasing the feedback level for a given deviation. This is applicable to modifying muscle activation patterns described below.

In some embodiments, individual tuning can be performed. For a particular wearer, a subset of the key parameters may provide effective at altering gait and/or reducing pain while the other parameters may have less or no effect. Therefore, the system, device, and method can track the wearer's gait kinematics improvement over time with each parameter and determine which parameters are most effective for that individual. This is applicable to modifying muscle activation patterns described below.

In some embodiments, the wearer's gait kinematics can be analyzed to determine which gait parameters are likely to be most relevant for a particular individual. For example, the deviations of key gait parameters from the ideal range can be determined, and the parameters with the largest deviations may be selected as the basis for the treatment.

In some embodiments, the wearer may be given different cues or stimulation, such as audio, vibratory, or electrical, to determine which cue or stimulation the wearer responds to the best, which the system and device can select for use during treatment. This is applicable to modifying muscle activation patterns described below.

In some embodiments, the data, which can be stored on the device or on an external device or the cloud, can be analyzed by a health care professional that can then modify the treatment in an open loop manner. The data can be accessed off the device during a follow up visit, by accessing the data on the cloud, or by sending the device back to the manufacturer to extract and transmit the data to the cloud or health care professional. In other embodiments, the system and device can analyze the data itself and modify treatment in a closed loop manner. This is applicable to modifying muscle activation patterns described below.

Method of Modifying Muscle Activation Patterns

In another embodiment, the wearable unit is in communication with an electrical stimulation unit that applies stimulation to a predetermined or predetermined set or subset of muscles that affect gait pattern (e.g., soleus, gastrocnemius, quadriceps) and a sensor unit that measures muscle activity (e.g., electromyogram (EMG)). The simulation unit and the sensor unit can be separate units in communication, wired or wireless, or housed in the same unit as shown in FIG. 18. For example, as shown in FIG. 18, an embodiment of the device that houses electrodes for EMG sensing 1802 and muscle stimulation 1800. The device can attach to the skin using an adhesive hydrogel 1804. The device can be applied to multiple locations on the lower extremity, including, but not limited to, the top of the foot, the head of the gastrocnemius, or above the knee across the quadriceps muscle group. Similar to devices and methods described below, the stimulation can be proportionally controlled based on measurements of voluntary EMG.

Reducing knee pain can be accomplished by reducing the load on the knee. Muscle forces are a large contributor to knee loads during walking, as shown in FIG. 21. Altering muscle forces during gait may reduce knee loads. For example, the gastrocnemius muscle is one of the largest contributors to knee load during walking, especially during late stance, and thus reducing the activation of the gastrocnemius muscle during late stance can reduce knee loads. In some embodiments, the load on the knee can be reduced by reducing an individual's activation of the gastrocnemius muscle, which extends from the femur to the heel and causes compression of the knee when it contracts, and optionally increasing an individual's activation of the soleus muscle, which extends from the tibia to the heel, does not cause compression of the knee when it contracts. FIGS. 22A-22C illustrate the location of the gastrocnemius 2200 and soleus 2202 muscles on the leg with respect to the knee 2204.

Since it is difficult for an individual to detect or control contraction of the gastrocnemius muscle relative to that of the soleus muscle, an EMG sensor can be used to detect and monitor contraction of the gastrocnemius and soleus muscles. When the EMG sensor detects use of the gastrocnemius muscle, feedback can be provided so the individual can reduce usage of the gastrocnemius muscle. When the EMG sensor detects use of the soleus muscle, a different feedback can be provided so the individual can increase the usage of the soleus muscle. The feedback can be detectable stimulation which can be auditory, vibratory, or electrical, for example. If EMG sensors are placed over both the gastrocnemius and the soleus, the two feedbacks can be different so that they are distinguishable by the individual. The feedback can be responsive and/or fading feedback as described herein with respect to FIGS. 17A and 17B. Such a system, device, and method provides motor learning or reprogramming therapy that can either train an individual to increase the use of the soleus and decrease the use of the gastrocnemius, or increase the excitability of the soleus and decrease the excitability of the gastrocnemius during gait, thereby reducing knee load.

In some embodiments, the system, device, and method can provide repetitive stimulation, which may be continuous for a period specified by the user (e.g., patient controlled on/off) or may be applied during a specific time of the day (i.e., daytime or known or scheduled activity period), to a desired muscle or muscles, such as the soleus, to enhance and increase the usage of this muscle during gait and/or to decrease or inhibit or reduce the usage of a muscle, such as the gastrocnemius, during gait. The stimulation can be timed with key gait events such as foot strike, toe off, early stance phase, and late stance phase, for example, which can be detected in real time by sensors during the gait cycle as described herein. Sensors can include EMG, IMU, or pressure sensors in the shoe or insoles or on the base of the foot, for example.

In some embodiments, the stimulation to inhibit or enhance the usage of muscles can be applied as constant or time stimulation during specific or predetermined activities that actively and/or passively engage the muscles of interest, such as stimulation of the tibial nerve and/or stimulations to identify gastrocnemius and soleus usage during exercise that engages the calf muscles, such as toe-raise exercises.

In some embodiments, a muscle or group of muscles can be inhibited or have its excitability reduced, such as the gastrocnemius, instead of or while the other muscle, such as the soleus, is optionally stimulated, in a reciprocal inhibition manner. For example, high frequency stimulation at the neuromuscular junction of the gastrocnemius can decrease the excitability of corticospinal tracts and lead to inhibition of the gastrocnemius and reduced knee load during walking. In some embodiments, the excitability of the gastrocnemius can be decreased by high frequency stimulation of a peripheral nerve such as the sciatic or tibial nerve to decrease excitability of its corticospinal tracts. In some embodiments, the excitability of the soleus can be increased by repeated peripheral stimulation of the tibial nerve. In some embodiments, the excitability of the soleus can be maintained or increased by exciting the peroneal nerve behind the knee or exciting the sural nerve in order to increase excitability of soleus motor neuron pool (as measured by means of the Hoffman reflex, or H reflex).

In some embodiments, the system, device, and method can alter gait kinematics and modify muscle activation for a combined treatment approach. This combined approach is particularly advantageous because changes in gait kinematics tend to have a greater effect on the peak knee load during the early stance phase (load generated after foot strike), which is shown as the first peak in FIGS. 23A and 23B, and changes in muscle generated force tend to have a greater effect on the peak knee load during the late stance phase (load generated prior to toe off), which is shown as the second peak in FIGS. 23A and 23B. FIG. 23 illustrates a reduction in knee load due to altering gait kinematics. Reduction is seen in the first peak of the curve during early stance. FIG. 23B illustrates a reduction in knee load due to reduction of muscle activation of gastrocnemius. Reduction is seen in the second peak of the curve during late stance.

Overall Framework

Treatment of a patient with knee pain from OA can be broken down into three phases: (1) diagnosis of the patient, (2) determining treatment based on the diagnosis, and (3) providing the treatment to the patient.

Diagnosis can include performing a diagnostic assessment of the patient using the wearable sensors described herein, such as IMU, accelerometers, pressure sensors, and EMG, to determine various gait parameters and muscle activation patterns, such as foot angle, knee angle, KAM, step width, gastrocnemius activation, and soleus activation. The patient can be provided (e.g., mail or pick up at doctor's office) with a kit with sensory prosthetics (e.g. wearable sensors) and optionally a video camera. In addition, video taken from a mobile phone or other camera (i.e., webcam, Kinect) can also be used to determine various gait parameters. During diagnosis, instructions can be provided to the patient to perform a predetermined series of tasks or actions, such as walking and/or toe raises, while using the sensors and/or video. Values and/or percentages can be assigned to each parameter or characteristic in order quantify its importance, which may be based on its magnitude or degree of deviation from an ideal range or value (degree of abnormality). The values and/or percentages can be used to identify and/or prioritize which parameters or characteristic needs the most correction. The patient can wear and use the sensors during the diagnostic phase for a predetermined or prescribed period of time (day, week, other interval). Data from the sensors can be uploaded to the cloud or another computing device, or the sensors can be sent back to the manufacturer for data analysis and then refurbished for a new patient.

The appropriate treatment for each patient can be determined based on the data generated by the diagnosis by a health care provider or by the processor unit of the system and device or by an external computing system. For example, high use of the gastrocnemius identified during diagnosis may indicate that the system and device should focus on training the patient to reduce use of the gastrocnemius. The diagnosis may also indicate that foot angle needs correction, but at a lower priority than gastrocnemius correction. In some embodiments, the treatment can be prescribed to focus on modifying one parameter or characteristic at a time, based on the priority identified during diagnosis, because it may be difficult for a patient to work on changing multiple parameters or characteristics simultaneously. In addition, working on a single parameter or characteristic may only require providing a single stimulation or cue, while working on multiple parameters or characteristics simultaneously would require providing multiple stimulations or cues that can be distinguished by the patient. The stimulation dosing can be optimized to promote or enhance motor and/or neural entrainment, using for example, responsive or proportional feedback/stimulation and/or fading feedback.

Once the treatment plan has been determined, the patient can be provided (e.g., mail or pick up at doctor's office) with the appropriate treatment system and device, which can be programmed to execute the treatment plan. The patient can be instructed, on a mobile phone app for example, on how and where to place the various components of the system and device on the patient's body. In some embodiments, the initial kit can include both the diagnostic sensors and treatment system and device, or the initial kit can include a system and device that performs both the diagnostic and treatment functions. In some embodiments, the system and device is designed to operate for a predetermined length of time, such as up to 30, 60, or 90 days, at which point the patient exchanges the old system and device with a new system and device. The old system and device can be returned to the manufacturer for refurbishing.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for reducing knee pain associated with osteoarthritis in an individual, the system comprising:
  at least one wearable sensor for measuring a plurality of gait parameters;
  one or more computing devices; and
  a therapy device in communication with the at least one wearable sensor,
  wherein the one or more computing devices are configured to track the plurality of gait parameters over time and select, based on an analysis of data, a chosen measured gait parameter determined to be most effective for reducing knee pain associated with osteoarthritis for the individual,
  wherein the therapy device is configured to deliver a sensory stimulation,
  wherein the one or more computing devices are configured to control the sensory stimulation based on the chosen measured gait parameter that is configured to alter the individual's gait, wherein the sensory stimulation has a stimulation parameter that is proportional to a deviation of the chosen measured gait parameter from a set range or value for the chosen measured gait parameter for the individual;
  wherein the sensory stimulation is configured by the one or more computing devices to reduce an excitability of a gastrocnemius muscle and enhance an excitability of a soleus muscle,
  wherein the sensory stimulation is configured by the one or more computing devices to retrain the gait of the individual such that the sensory stimulation is provided less frequently or at a decreased intensity level until the sensory stimulation is no longer needed, and
  wherein at least a portion of the analysis is performed using data stored on a cloud server.

2. The system of claim 1, wherein the sensory stimulation is electrical and is configured to not induce contraction of a muscle.

3. The system of claim 1, wherein the sensory stimulation is configured to enhance motor plasticity.

4. The system of claim 1, wherein the sensory stimulation is tactile or auditory.

5. The system of claim 1, wherein the at least one wearable sensor comprises an IMU or a force sensor.

6. The system of claim 1, wherein the plurality of gait parameters is at least one of foot progression angle, toe angle, ankle plantar flexion angle, step width, knee flexion angle, knee adduction angle, or knee adduction moment, knee flexion moment, or ankle plantar flexion moment, or any combination of these gait parameters.

7. The system of claim 1, wherein the at least one wearable sensor and/or therapy device comprises a knee band, ankle band, leg band, sock, knee brace, ankle brace, shoe, insole, compliant patch, pants, leg sleeve, knee sleeve, ankle sleeve, knee wrap, foot wrap, ankle wrap, or shoe attachment.

8. A system for reducing knee pain associated with osteoarthritis in an individual, the system comprising:
    a first wearable EMG sensor configured for measuring a plurality of gait parameters indicative of an activation of a gastrocnemius muscle;
    a second wearable EMG sensor configured for measuring a plurality of gait parameters indicative of an activation of a soleus muscle;
    one or more computing devices; and
    a therapy device in communication with the first and second wearable EMG sensors,
    wherein the one or more computing devices are configured to analyze the plurality of gait parameters from the first wearable EMG sensor and the second wearable EMG sensor and select, based on the analysis, a selected gait parameter from the plurality of gait parameters determined to be most relevant for altering the gait of the individual, wherein the analysis includes determining deviations of the plurality of gait parameters from an ideal range for the individual,
    wherein the therapy device is configured to deliver sensory stimulations,
    wherein the one or more computing devices are configured to control the sensory stimulations based on the selected gait parameter indicative of activation of the gastrocnemius muscle and the soleus muscle,
    wherein the sensory stimulations are configured by the one or more computing devices to provide feedback to reduce the activation of the gastrocnemius muscle and enhance the activation of the soleus muscle, and
    wherein the sensory stimulations are configured by the one or more computing devices to retrain gait such that the sensory stimulations are provided less frequently or at a decreased intensity level until the sensory stimulations are no longer needed.

9. The system of claim 8, further comprising a wearable sensor for measuring a gait event.

10. The system of claim 9, wherein the gait event is selected from the group consisting of foot strike and toe off.

11. The system of claim 9, wherein the therapy device is configured to deliver the stimulations based on the measured activation.

12. The system of claim 9, wherein the therapy device is configured to deliver the stimulation configured to enhance the activation of the soleus muscle based on the measured activation.

13. A system for reducing knee pain associated with osteoarthritis in an individual, the system comprising:
    at least one wearable sensor for measuring a plurality of gait parameters;
    one or more computing devices, wherein the one or more computing devices are configured to analyze the plurality of gait parameters from the at least one wearable sensor and select, based on the analysis, a selected gait parameter of the plurality of gait parameters that is determined to be most effective at altering the gait of the individual,
    a wearable EMG sensor for measuring an activation of a gastrocnemius muscle; and
    a therapy device configured for communication with the at least one wearable sensor and the wearable EMG sensor, the therapy device configured to deliver a first sensory stimulation and a second sensory stimulation, wherein the one or more computing devices are configured to control the first sensory stimulation based on the selected gait parameter and to control the second sensory stimulation based on the measured activation of the gastrocnemius muscle, wherein the first sensory stimulation has a stimulation parameter that is proportional to a deviation of the selected-gait parameter from a set range or value for the selected gait parameter, wherein the second sensory stimulation is configured to inform the individual to reduce the activation of the gastrocnemius muscle,
    wherein the first and second sensory stimulations are configured by the one or more computing devices to retrain gait such that the first and second sensory stimulations are provided less frequently or at a decreased intensity level until the first and second sensory stimulations are no longer needed; and
    wherein at least a portion of the analysis is performed on a cloud server or external computing device of the one or more computing devices separate from the therapy device.

14. The system of claim 13, wherein the therapy device is configured to deliver a fourth stimulation configured to enhance the activation of a soleus muscle.

15. A system for reducing knee pain associated with osteoarthritis in an individual, the system comprising:
    a plurality of wearable sensors for measuring a plurality of gait parameters;
    one or more computing devices;
    wherein the one or more computing devices are configured to track the plurality of gait parameters over time and select, based on the tracking, a subset of gait parameters of the plurality of gait parameters that are likely to be most effective at reducing knee pain associated with osteoarthritis in the individual,
    wherein at least one of the subset of gait parameters is a foot angle;
    a wearable EMG sensor for measuring an activation of a soleus muscle; and
    a therapy device in communication with the plurality of wearable sensors and the wearable EMG sensor, the therapy device configured to deliver a first sensory stimulation and a second sensory stimulation, wherein the one or more computing devices are configured to control the first sensory stimulation based on the foot angle that is configured to alter the individual's gait and to control the second sensory stimulation based on the measured activation of the soleus muscle, wherein the first sensory stimulation has a stimulation parameter that is proportional to a deviation of the foot angle from a set range or value for the individual, wherein the second sensory stimulation is configured to inform the individual to increase activation of the soleus muscle, and wherein the first and second sensory stimulations are configured by the one or more computing devices to retrain gait such that the first and second sensory stimulations are provided less frequently or at a decreased intensity level until the first and second sensory stimulations are no longer needed.

16. The system of claim 15, wherein the therapy device is configured to deliver a third stimulation configured to enhance the activation of the soleus muscle.

17. The system of claim 16, wherein the therapy device is configured to deliver a fourth stimulation configured to reduce activation of a gastrocnemius muscle.

\* \* \* \* \*